(12) United States Patent
Staub et al.

(10) Patent No.: US 6,781,033 B2
(45) Date of Patent: Aug. 24, 2004

(54) METHOD FOR THE TRANSFORMATION OF PLANT CELL PLASTIDS

(75) Inventors: Jeffrey M Staub, Wildwood, MO (US); Guangning Ye, Ellisville, MO (US); Debra L. Broyles, Wright City, MO (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 09/843,324

(22) Filed: Apr. 25, 2001

(65) Prior Publication Data

US 2002/0042934 A1 Apr. 11, 2002

Related U.S. Application Data

(60) Provisional application No. 60/199,774, filed on Apr. 26, 2000.

(51) Int. Cl.[7] .................................................. A01H 1/00
(52) U.S. Cl. ........................................ 800/278; 800/288
(58) Field of Search ................................. 800/278, 288, 800/300; 435/468, 418, 419, 430, 470

(56) References Cited

FOREIGN PATENT DOCUMENTS

| GB | 2 183 660 | 6/1987 |
|----|-----------|--------|
| WO | WO 99 05265 | 2/1999 |
| WO | WO 99 10513 | 3/1999 |
| WO | WO 00 03022 | 1/2000 |
| WO | WO 01 04327 | 1/2001 |

OTHER PUBLICATIONS

Daniel H et al., "Containment of herbicide resistance through genetic engineering of the chloroplast genome," Nature Biotechnology, Nature Publishing (US), p. 345–48, (Apr. 1998).

Daniel H et al., "The next generation of genetically engineered crops for herbicide and insect resistance: containing of gene pollution and resistant insects," AgBiotechNet, vol. 1 (No. 24), p. 8–24, (Aug. 1999).

Lutz Kerry A et al., "Expression of bar in the plastid genome confers herbicide resistance," Plant Physiology, vol. 125 (No. 4), p. 1585–90, (Apr. 2001).

Przibilla E et al., "Site specific mutagenesis of the D1 subunit of photosystem II in wild-type chlamydomonas," Plant Cell, vol. 3 (No. 2), p. 169–74, (1991).

Ye Guangning et al., "Plastid-expressed 5-enolpyruvylshikimate-3-phosphate synthase genes provide high level glyphosate tolerance in tobacco," Plant Journal, vol. 25 (No. 3), p. 261–70, (Feb. 2001).

Primary Examiner—Anne Kubelik
(74) Attorney, Agent, or Firm—Thomas P. McBride

(57) ABSTRACT

Novel compositions and methods useful for genetic engineering of plant cells to provide a method of producing plastid transformed plants are provided in the instant invention. In particular, the present invention provides methods for obtaining plastid transformed plants on medium containing plastid lethal compounds.

6 Claims, 22 Drawing Sheets

Glyphosate - 50ppm 1 week  Figure 2

Glyphosate - 50 ppm 4 weeks  Figure 3

Glyphosate -200 ppm 1 week   Figure 4

Glyphosate - 200 ppm 4 weeks  Figure 5

Spectinomycin - 500 ppm
4 weeks

Spectinomycin – 500 ppm
4 weeks

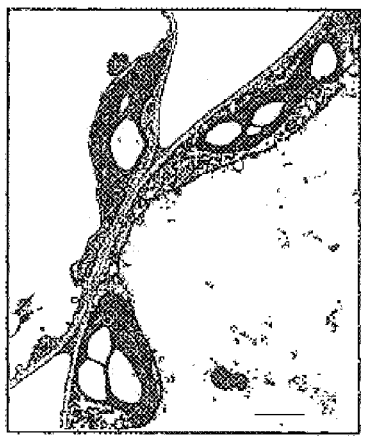
*Phosphinothricin - 4 mg/L - 3 days*
Figure 13
*Phosphinothricin - 4 mg/L - 7 days*
Figure 14
*Phosphinothricin - 4 mg/L - 12 days*
Figure 15

Fig. 16A
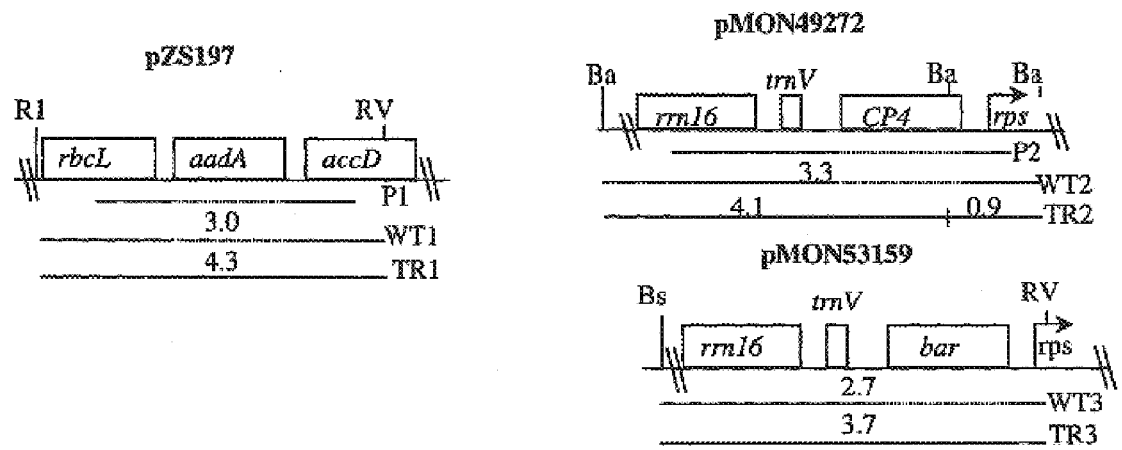
Fig. 16B  aadA region probe
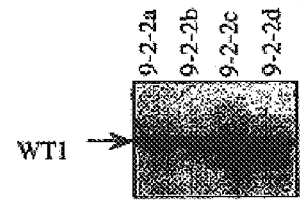

Fig. 16C  CP4 region probe
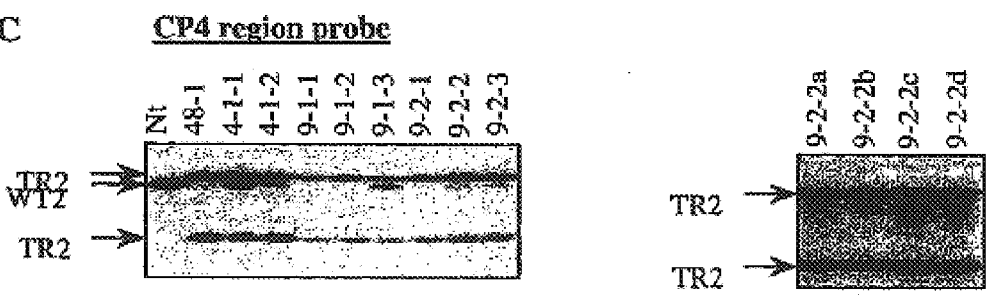
Fig. 16D  aadA region probe
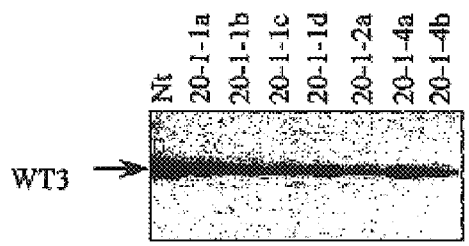
Fig. 16E  bar region probe
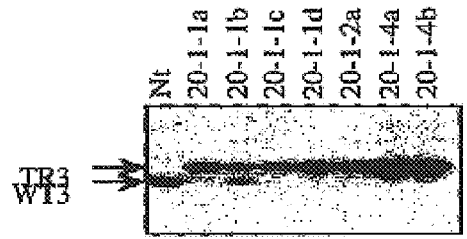

| # shots | # Gly selected | # analyzed | # CP4+ |
|---|---|---|---|
| 60 | 7 | 6 | 6 |

# METHOD FOR THE TRANSFORMATION OF PLANT CELL PLASTIDS

This application claims priority to U.S. Provisional Application 60/199,774, filed Apr. 26, 2000, herein incorporated by reference in its entirety.

INTRODUCTION

1. Technical Field

This invention relates to the application of genetic engineering techniques to plants. Specifically, the invention relates to compositions and methods for transformation of nucleic acid sequence into plant cell plastids.

2. Background

Molecular biological techniques have enabled researchers to introduce pieces of DNA from one organism to another organism. Such techniques, referred to as recombinant DNA technology, have positively impacted the areas of medicine and agriculture. Conventional cloning methods have enabled the introduction of new pharmaceuticals and improved crops of agricultural importance. As the need for the introduction of multiple pieces of DNA and larger fragments of DNA into numerous target hosts increases, the need for novel cloning strategies increases accordingly.

The plastids of higher plants are an attractive target for genetic engineering. Plant plastids (chloroplasts, amyloplasts, elaioplasts, chromoplasts, etc.) are the major biosynthetic centers that in addition to photosynthesis are responsible for production of industrially important compounds such as amino acids, complex carbohydrates, fatty acids, and pigments. Plastids are derived from a common precursor known as a proplastid and thus the plastids present in a given plant species all have the same genetic content. Plant cells contain 500–10,000 copies of a small 120–160 kilobase circular genome, each molecule of which has a large (approximately 25 kb) inverted repeat. Thus, it is possible to engineer plant cells to contain up to 20,000 copies of a particular gene of interest which potentially can result in very high levels of foreign gene expression.

Previous studies directed to stable transformation of plant chloroplasts have relied on homologous recombination to incorporate desired gene constructs into plastids using spectinomycin as the selectable marker for selection of transplastomic plants. However, at present, methods for multiple rounds of plastid transformation (for example for gene stacking) are restricted due to the limited number of selectable markers described for plastid transformation. Thus, there is a need in the art for methods employing additional selectable markers for obtaining plastid transformed plants.

SUMMARY OF THE INVENTION

By this invention, methods for obtaining plants having transformed plastids are provided. Specifically, methods are provided for obtaining plants having transformed plastids by selection of plastid transformed cells on medium containing a plastid lethal compound.

A first aspect of the present invention provides constructs useful for obtaining transplastomic plants. The constructs generally comprise a promoter functional in a plant cell plastid and a nucleic acid sequence encoding a protein that provides resistance to plastid lethal compounds.

Another aspect of the present invention is to provide methods for obtaining transplastomic plants using a nucleic acid sequence encoding a protein that provides resistance to plastid lethal compounds.

A further aspect of the present invention provides methods for obtaining transplastomic plants on selective medium containing glyphosate.

Also provided in the present application are methods for obtaining plastid transformed plants on selective medium containing phosphinothricin.

In yet another aspect of the present invention, methods for regenerating a plant having transformed plastids on medium containing plastid lethal compounds are provided.

The present invention also provides methods for the regeneration of a plant from a plant cell by growing the plant on medium containing plastid lethal compounds.

Another aspect of the present invention provides a method of obtaining a plastid transformed plant that does not contain an introduced nucleic acid sequence encoding a gene providing resistance to an antibiotic.

In a further aspect, methods for transforming the plastids of a host plant cell plastid are provided. The method generally comprises introducing into a plant cell plastid a first construct having a promoter functional in a plant cell plastid, a nucleic acid sequence encoding a protein that provides tolerance to a plastid lethal compound and a transcriptional termination region functional in a plant cell plastid. Additional expression cassettes can also be introduced, such cassettes having a promoter functional in a plant cell plastid, a nucleic acid sequence encoding a protein that provides tolerance to plastid non-lethal compounds, and a transcriptional termination region. Plant cells having the introduced construct or constructs are then grown on a first medium containing a plastid non-lethal compound for a time period sufficient to permit plastids containing the construct that provides resistance to a plastid lethal compound to increase in number, and then removed from the first medium and placed on a second medium containing a plastid lethal compound to permit selection of those transplastomic plant cells expressing the protein conferring tolerance to the plastid lethal compound.

In yet a further aspect, methods for transforming the plastids of a host plant cell plastid are provided. The method generally comprises introducing into a plant cell plastid a first construct having a promoter functional in a plant cell plastid, a nucleic acid sequence encoding a protein that provides tolerance to a plastid lethal compound and a transcriptional termination region functional in a plant cell plastid. Plant cells having the introduced construct are then grown on a first medium containing a sublethal concentration of a plastid lethal compound for a period of time sufficient to permit transformed plastids in transplastomic plant cells to increase in number as compared to non-transformed plastids, and then removed from such first medium and placed on a second medium containing a lethal concentration of a plastid lethal compound to permit selection of those transplastomic plant cells expressing the protein conferring tolerance to the plastid lethal compound.

Also considered in the present invention are the plant cells and plants produced by the methods described herein.

DESCRIPTION OF THE FIGURES

FIG. 13 provides transmission electron micrographs of tissues treated for 3 days on phosphinothricin (PPT), demonstrating the effect on plastid ultrastructure. Thylakoid membranes are completely absent and the stromal contents are densely stained, indicating a tight packing of accumulated toxic compounds. Starch is present, but less than in wild-type cells. The outer plastid membrane is also apparently missing in some places, and some membranous structures that are possibly thylakoid remnants are leaked into the cell cytosol.

FIG. 14 provides transmission electron micrographs of thin sections of tissue treated for 7 days with 4 mg/L phosphinothricin showing oil bodies containing toxic compounds accumulated in the organelles. Starch granules are very small and dispersed.

FIG. 15 provides transmission electron micrographs of thin sections of tissue treated for 12 days with 4 mg/L phosphinothricin showing oil bodies containing toxic compounds accumulated in the organelles. Starch granules are very small and dispersed.

FIGS. 16A–E provides an example of Southern blot hybridizations to detect CP4+ segregants or bar+ segregants after transformations with plasmids pZS197 and pMON49272, or pZS197 and pMON53159, respectively.

DETAILED DESCRIPTION OF THE INVENTION

In accordance with the subject invention, constructs and methods are provided for obtaining plastid transformed plants on medium containing a plastid lethal compound. The methods of the present invention provide a novel means for obtaining transplastomic plants.

The following definitions and methods are provided to better define, and to guide those of ordinary skill in the art in the practice of, the present invention. Unless otherwise noted, terms are to be understood according to conventional usage by those of ordinary skill in the relevant art. The nomenclature for DNA bases as set forth at 37 CFR § 1.822 is used. The standard one- and three-letter nomenclature for amino acid residues is used.

As used herein a "plastid lethal compound" refers to any compound affecting the viability of a wild-type plant cell plastid. Compounds affecting the viability of a wild-type plant cell plastid include, but are not limited to, compounds that rapidly degrade plastid membranes, inhibit plastidial metabolic pathways (such as aromatic amino acid biosynthesis, photosynthesis, chlorophyll biosynthesis, ammonium assimilation, and the like), toxic compounds, proteases, nucleases, compounds that alter the pH of the cell, and the like. Preferably, the plastid lethal compound degrades the inner and outer membranes of a wild-type plant cell plastid. Most preferably, a plastid lethal compound promotes degradation of the wild-type (wt) plastidial membranes within 14 days of administration, preferably, within 10 days, more preferably, within 7 days of administration. Such compounds include any compound that disintegrates the inner and outer membranes of the plastid. Examples of such compounds include any herbicide, which includes but is not limited to glyphosate, phosphinothricin, norflurazone, atrazine, glufosinate, bromoxynil, and acifluorfen.

The skilled artisan will recognize that the ability of plastid lethal compounds to affect plastid viability is dependent upon the concentration of the compound in the medium, the length of time of exposure, and the plant tissue type and/or source. For example, using a low concentration of a given plastid lethal compound can render the compound non-lethal. As used herein, "sublethal concentrations" of a plastid lethal compound refers to the use of an amount of a plastid-lethal compound as to not affect the viability of a wild-type plant cell plastid in less than about 12 weeks of exposure depending on the tissue source and tissue type. Preferably, the sublethal concentration of a plastid lethal compound will not affect the viability of a wild-type plant cell plastid in less than about 8 weeks of exposure, more preferably in less than 6 weeks of exposure, preferably in less than 4 weeks of exposure, most preferably in less than 3 weeks of exposure, most especially preferable in less than 2 weeks of exposure.

Figure 11:
FIG. 11 provides transmission electron micrographs of tissues obtained from plants treated for one week with 500 mg/L spectinomycin showing that the plastids look relatively normal. Thylakoid membranes and grana are present, along with starch granules.

As used herein, the term "plastid non-lethal compound" refers to compounds that affect the metabolism of the plant cell plastid and therefore slow or inhibit growth of the plastid or the cell as a whole but do not affect the viability of the plastid or the plant cell during the initial phase. However, exposure to such compounds at higher concentrations and/or for longer periods of time can affect the viability of the plant cell plastid. For example, spectinomycin inhibits protein synthesis in the plastid and therefore growth is slowed, but spectinomycin does not disrupt the plastid initially (FIG. 11). Over a long period of time, spectinomycin will affect the viability of the plastid and the plant cell (FIGS. 12A and B), but it is a slow process as opposed to the faster, more disruptive process of the plastid lethal compounds. The preferred concentrations of the plastid non-lethal compound will depend upon the tissue type and source as well as the compound employed. The period of exposure to the plastid non-lethal compound does not affect the viability of the plant cell plastid in less than 12 weeks of exposure, preferably in less than 8 weeks of exposure, more preferably in less than 4 weeks of exposure, most preferably in less than 3 weeks of exposure, most especially preferably in less than 2 weeks of exposure. Examples of plastid non-lethal compounds include but are not limited to streptomycin, spectinomycin, lincomycin, paromomycin, and kanamycin.

A first nucleic acid sequence is "operably linked" with a second nucleic acid sequence when the sequences are so arranged that the first nucleic acid sequence affects the function of the second nucleic-acid sequence. Preferably, the two sequences are part of a single contiguous nucleic acid molecule and more preferably are adjacent. For example, a promoter is operably linked to a gene if the promoter regulates or mediates transcription of the gene in a cell.

A "recombinant" nucleic acid is made by an artificial combination of two otherwise separated segments of sequence, e.g., by chemical synthesis or by the manipulation of isolated segments of nucleic acids by genetic engineering techniques. Techniques for nucleic-acid manipulation are well-known (see for example Sambrook et al., Molecular Cloning: A Laboratory Manual, Cold Spring Harbor Press, 1989; Mailga et al., Methods in Plant Molecular Biology, Cold Spring Harbor Press, 1995; Birren et al., Genome Analysis: volume 1, Analyzing DNA, (1997), volume 2, Detecting Genes, (1998), volume 3, Cloning Systems, (1999) volume 4, Mapping Genomes, (1999), Cold Spring Harbor, N.Y.).

Methods for chemical synthesis of nucleic acids are discussed, for example, in Beaucage and Carruthers, Tetra. Letts. 22:1859–1862, 1981, and Matteucci et al., J. Am. Chem. Soc. 103:3185, 1981. Chemical synthesis of nucleic acids can be performed, for example, on commercial automated oligonucleotide synthesizers.

A "synthetic nucleic acid sequence" can be designed and chemically synthesized for enhanced expression in particular host cells and for the purposes of cloning into appropriate vectors. Host cells often display a preferred pattern of codon usage (Campbell et al., Plant Physiol., 92: 1–11, 1990). Synthetic DNAs designed to enhance expression in a particular host should therefore reflect the pattern of codon usage in the host cell. Computer programs are available for these purposes including but not limited to the "BestFit" or "Gap" programs of the Sequence Analysis Software Package, Genetics Computer Group, Inc., University of Wisconsin Biotechnology Center, Madison, Wis. 53711.

"Amplification" of nucleic acids or "nucleic acid reproduction" refers to the production of additional copies of a nucleic acid sequence and is carried out using polymerase chain reaction (PCR) technologies. A variety of amplification methods are known in the art and are described, inter alia, in U.S. Pat. Nos. 4,683,195 and 4,683,202 and in PCR Protocols: A Guide to Methods and Applications, ed. Innis et al., Academic Press, San Diego, 1990. In PCR, a primer refers to a short oligonucleotide of defined sequence that is annealed to a DNA template to initiate the polymerase chain reaction.

"Transformed", "transfected", or "transgenic" refers to a cell, tissue, organ, or organism into which has been introduced a foreign nucleic acid, such as a recombinant vector. Preferably, the introduced nucleic acid is integrated into the genomic DNA of the recipient cell, tissue, organ or organism such that the introduced nucleic acid is inherited by subsequent progeny. A "transgenic" or "transformed" cell or organism also includes progeny of the cell or organism and progeny produced from a breeding program employing such a "transgenic" plant as a parent in a cross and exhibiting an altered phenotype resulting from the presence of a recombinant construct or vector.

The term "gene" refers to chromosomal DNA, plasmid DNA, cDNA, synthetic DNA, or other DNA that encodes a peptide, polypeptide, protein, or RNA molecule, and regions flanking the coding sequence involved in the regulation of expression. Some genes can be transcribed into mRNA and translated into polypeptides (structural genes); other genes can be transcribed into RNA (e.g., rRNA, tRNA); and other types of genes function as regulators of expression (regulator genes).

"Expression" of a gene refers to the transcription of a gene to produce the corresponding mRNA and translation of this mRNA to produce the corresponding gene product, i.e., a peptide, polypeptide, or protein. Gene expression is controlled or modulated by regulatory elements including 5' regulatory elements such as promoters.

"Genetic component" refers to any nucleic acid sequence or genetic element that may also be a component or part of an expression vector. Examples of genetic components include, but are not limited to, promoter regions, 5' untranslated leaders, introns, genes, 3' untranslated regions, and other regulatory sequences or sequences that affect transcription or translation of one or more nucleic acid sequences.

The terms "recombinant DNA construct", "recombinant vector", "expression vector" or "expression cassette" refer to any agent such as a plasmid, cosmid, virus, BAC (bacterial artificial chromosome), autonomously replicating sequence, phage, or linear or circular single-stranded or double-stranded DNA or RNA nucleotide sequence, derived from any source, capable of genomic integration or autonomous replication, comprising a DNA molecule in which one or more DNA sequences have been linked in a functionally operative manner using well-known recombinant DNA techniques.

"Plastid lethal construct" or "plastid lethal expression construct" refers to any "expression cassette" that provides for the expression of a recombinant nucleic acid sequence encoding for a gene that provides tolerance to a plastid lethal compound.

"Plastid non-lethal construct" or "plastid non-lethal expression construct" refers to any "expression cassette" that provides for the expression of a recombinant nucleic acid sequence encoding for a gene that provides tolerance to a plastid non-lethal compound.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species, or, if from the same species, is substantially modified from its original form by deliberate human intervention.

As used herein, "recombinant" includes reference to a cell or vector that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention.

By "host cell" is meant a cell that contains a vector and supports the replication, and/or transcription or transcription and translation (expression) of the expression construct. Host cells for use in the present invention can be prokaryotic cells, such as *E. coli*, or eukaryotic cells such as yeast, plant, insect, amphibian, or mammalian cells. Preferably, host cells are monocotyledenous or dicotyledenous plant cells.

As used herein, the term "plant" includes reference to whole plants, plant organs (for example, leaves, stems, roots, etc.), seeds, and plant cells and progeny of same. Plant cell, as used herein includes, without limitation, seed suspension cultures, embryos, meristematic regions, callus tissue, leaves, roots, shoots, gametophytes, sporophytes, pollen, and microspores. The class of plants that can be used in the methods of the present invention is generally as broad as the class of higher plants amenable to transformation techniques, including both monocotyledenous and dicotyledenous plants. Particularly preferred plants include Acacia, alfalfa, aneth, apple, apricot, artichoke, arugula, asparagus, avocado, banana, barley, beans, beet, blackberry, blueberry, broccoli, brussels sprouts, cabbage, canola, cantaloupe, carrot, cassava, cauliflower, celery, cherry, chicory, cilantro, citrus, clementines, coffee, corn, cotton, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, mango, melon, mushroom, nectarine, nut, oat, oil palm, oil seed rape, okra, onion, orange, an ornamental plant, papaya, parsley, pea, peach, peanut, pear, pepper, persimmon, pine, pineapple, plantain, plum, pomegranate, poplar, potato, pumpkin, quince, radiata pine, radicchio, radish, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini.

As used herein, "transgenic plant" includes reference to a plant that comprises within its nuclear genome a heterologous polynucleotide. Generally, the heterologous polynucleotide is stably integrated within the nuclear genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "transplastomic" refers to a plant cell having a heterologous nucleic acid introduced into the plant cell plastid. The introduced nucleic acid may be integrated into the plastid genome, or may be contained in an autonomously replicating plasmid. Preferably, the nucleic acid is integrated into the plant cell plastid's genome. A plant cell can be both transgenic and transplastomic.

The term "introduced" in the context of inserting a nucleic acid sequence into a cell, means "transfection", or "transformation" or "transduction" and includes reference to the incorporation of a nucleic acid sequence into a eukaryotic or prokaryotic cell where the nucleic acid sequence may be incorporated into the genome of the cell (for example, chromosome, plasmid, plastid, or mitochondrial DNA), converted into an autonomous replicon, or transiently expressed (for example, transfected mRNA).

In one embodiment of the present invention, methods are provided employing recombinant nucleic acid constructs that provide for the expression of a nucleic acid sequence encoding a protein that provides resistance to plastid lethal compounds. In general, the constructs comprise at least one expression cassette having a promoter functional in a plant cell plastid and a nucleic acid sequence encoding a protein that provides tolerance to a plastid lethal compound. The construct may also contain one or more additional expression cassettes having a promoter functional in a plastid, a nucleic acid sequence of interest and a transcriptional termination region.

In one important aspect of the present invention, transplastomic plants are obtained from host plant cells into which a recombinant nucleic acid construct conferring tolerance to a plastid lethal compound has been introduced. The method for obtaining the transplastomic plant of the present invention generally involves culturing transplastomic plant cells on culture medium in two phases.

The first phase involves the growth of transplastomic plant cells on a first culture medium containing a plastid non-lethal compound or a sublethal concentration of a plastid lethal compound. Generally, the transplastomic plant tissue is then transferred to a second culture media containing an inhibitory amount of the corresponding plastid lethal selective agent, as well as the particular hormones and other substances necessary to obtain regeneration for that particular plant species. This first phase of selection allows for continued growth and replication of transplastomic plant cells containing constructs for the expression of genes providing tolerance to plastid lethal compounds so that such transplastomic plant cells may be selected in the second phase of the process.

Thus, the first phase generally involves the amplification or replication of the transformed plastids under plastid non-lethal conditions. For example, plant cells into which recombinant nucleic acid constructs have been introduced into the plastid can be cultured on a plastid non-lethal compound for a period of time allowing for the transformed plastids to increase in number, as compared to the non-transformed plastids. Alternatively, the transformed plant cell can be cultured on a medium containing a sublethal concentration of a plastid lethal compound. After the first phase of the process, the transplastomic plant cells are transferred to a second medium for the second phase of selection and regeneration.

The second phase of selection and regeneration generally involves culturing the transplastomic plant cells on a second culture medium that contains a plastid lethal compound. Under such conditions, plastids expressing a gene conferring tolerance to plastid lethal compounds are selected.

Thus, the plant cells having transformed plastids that have been first cultured for a period of time allowing for the proliferation of the transformed plastids on the first medium are now cultured or grown on a medium containing an inhibitory amount of a plastid lethal compound. Only those plant cells expressing the protein conferring tolerance to the plastid lethal compound will continue to grow and may be selected and regenerated into whole plants.

Thus, another aspect of the present invention provides methods for obtaining transplastomic plants using a "two phased" selection process. The method generally involves the introduction of two expression constructs into a plant cell plastid. One construct provides for the expression of a nucleic acid sequence encoding a protein that provides tolerance to plastid non-lethal compounds. The second construct provides for the expression of a protein providing tolerance to a plastid lethal compound. Cells into which the constructs have been introduced are first cultured under conditions that allow for the replication of the transformed plastids, referred to as "phase one" culture. Phase one involves culturing plant cells on medium containing a plastid non-lethal compound. Transplastomic cells from phase one culturing are transferred to a second medium containing an inhibitory amount of a plastid-lethal compound for regeneration of plant shoots. Thus, only those transplastomic plant cells containing the construct providing tolerance to the plastid-lethal compound are selected. Subsequent rounds of regeneration of transplastomic cells on medium containing the plastid-lethal compound leads to the selection and identification of homoplasmic plant lines.

The two plastid expression constructs employed preferably contain regions of homology for integration into the host cell plastid genome. The regions of homology used can target the constructs to any location in the plastid genome. Furthermore, the regions of homology can target the constructs to either the same location in the plastid genome, or to different locations in the plastid genome.

Where the regions of homology used target the introduced expression constructs to different locations in the plastid genome, several populations of plastid genomes are possible. For example, transformed plastids can contain both plastid expression constructs integrated into the genome. Alternatively, the genomes can contain one or the other of the integrated expression constructs, or the genomes may not contain a recombinant expression construct at all. During phase one selection, plastid genomes are able to replicate and increase in numbers. After transfer to selection medium containing plastid lethal compounds in phase two of selection, only plastids comprising genomes containing the construct providing for tolerance to plastid lethal compounds will be selected. Thus, the plant cells containing untransformed plastids and the transplastomic plant cells containing only plastids transformed with the plastid non-lethal construct will be selected against. The transplastomic plant cells thus arising on phase two selection will yield transplastomic plants containing plastids having either a single construct insert providing expression of the gene providing tolerance to a plastid lethal compound or both introduced constructs providing expression of the genes providing tolerance to a plastid non-lethal and plastid lethal compound. Transplastomic plants can then be analyzed, used for additional rounds of plant regeneration to obtain homoplasmy, and, if desired, selected for the single construct insertion.

Constructs employing the same regions of homology yield cells having plastid populations having either the plastid lethal construct, the plastid non-lethal construct, or untransformed plastids. The phased selection procedures as described in the previous scheme is followed, however, phase two selections yields transplastomic plants carrying plastids with only the construct providing tolerance to the plastid lethal compound because both introduced genes can not reside on the same genome. As a consequence of the phased selection method, the gene conferring tolerance to the plastid non-lethal compound is lost.

In addition, for the two phased selection method, if segregation of the two expression cassettes is not necessary or desirable, the constructs may be prepared to direct the integration of the plastid lethal construct and the plastid non-lethal construct on the same nucleic acid fragment between a single set of plastid regions of homology.

Also provided in the methods of the present invention are methods for the direct selection of transplastomic plant cells by selection on a medium containing a plastid lethal compound. The method generally involves a two-step procedure involving, first, growing transplastomic plant cells on a first medium containing a sublethal concentration of a plastid lethal compound, followed by growth and selection on a second medium containing a lethal concentration of the plastid lethal compound. During the second step of the selection process, transplastomic plant cells containing transformed plastids are selected on the basis of its ability to express the protein conferring tolerance to the plastid lethal compound. Subsequent rounds of selection on medium containing a lethal or inhibitory amount of the plastid lethal compound leads to the identification and production of homoplasmic lines containing the plastid lethal construct.

Transplastomic plants may be analyzed for a pure population of transformed plastid genomes (homoplasmic lines). Homoplasmy can be verified using Southern analysis employing nucleic acid probes spanning a region of the transgene and chloroplast genome (i.e., the insertion region). Transplastomic plants that are heteroplasmic (i.e., contain a mixture of plastid genomes containing and lacking the transgene) are characterized by a hybridization pattern of wild-type and transgenic bands. Homoplasmic plants show a hybridization pattern lacking the wild-type band.

Alternatively, homoplasmy may be verified using the polymerase chain reaction (PCR). PCR primers are utilized that are targeted to amplify from sequences from the insertion region. For example, a pair of primers may be utilized in a PCR reaction. One primer amplifies from a region in the transgene, whereas the second primer amplifies from a region proximal to the insertion region towards the insertion region. A second PCR reaction is performed using primers designed to amplify the region of insertion. Transplastomic lines identified as homoplasmic produce the expected size fragment in the first reaction, whereas they do not produce the predicted size fragment in the second reaction.

In a preferred embodiment of the direct selection aspect of the present invention, glyphosate is utilized as the selection agent to identify transplastomic plants comprising a nucleic acid construct containing a promoter functional in a plant cell plastid, a nucleic acid sequence encoding a protein conferring glyphosate tolerance, and a transcriptional termination sequence. As demonstrated in Example 1 below, glyphosate is a plastid lethal compound. Transformation of one or a few copies of the chloroplast genome in a particular plant cell may not, however, provide sufficient tolerance to glyphosate to select for such transplastomic plant cells during the initial period after transformation. Therefore, transplastomic transformed plant cells comprising the construct conferring glyphosate tolerance are placed on a first medium containing a sublethal amount of glyphosate for a period of time sufficient to permit transplastomic plant cells containing the construct to increase in number. The transplastomic plant cells then containing a sufficient number of plastid genomes carrying the construct conferring glyphosate tolerance are transferred to a second medium containing a lethal concentration of a plastid lethal compound whereby transplastomic plant cells conferring tolerance to glyphosate may be selected. In this manner, it is possible to obtain transplastomic plants directly on medium containing glyphosate.

In developing the constructs of the instant invention, the various fragments comprising the regulatory regions and open reading frame may be subjected to different processing conditions, such as ligation, restriction enzyme digestion, PCR, in vitro mutagenesis, linkers and adapters addition, and the like. Thus, nucleotide transitions, transversions, insertions, deletions, or the like, may be performed on the DNA that is employed in the regulatory regions, the nucleic acid sequences of interest for expression in the plastids. Methods for restriction digests, Klenow blunt end treatments, ligations, and the like are well known to those in the art and are described, for example, by Maniatis et al. (in *Molecular cloning: a laboratory manual* (1982) Cold Spring Harbor Laboratory Press, Cold Spring Harbor, N.Y.).

During the preparation of the constructs, the various fragments of DNA will often be cloned in an appropriate cloning vector, which allows for amplification of the DNA, modification of the DNA or manipulation by joining or removing of sequences, linkers, or the like. Normally, the vectors will be capable of replication in at least a relatively high copy number in *E. coli*. A number of vectors are readily available for cloning, including such vectors as pBR322, pUC series, M13 series, and pBluescript (Stratagene; La Jolla, Calif.).

The constructs for use in the methods of the present invention are prepared to direct the expression of the nucleic acid sequences directly from the host plant cell plastid. Examples of such constructs and methods are known in the art and are generally described, for example, in Svab et al. (1990) *Proc. Natl. Acad. Sci. USA* 87:8526–8530 and Svab and Maliga (1993) *Proc. Natl. Acad. Sci. USA* 90:913–917 and in U.S. Pat. No. 5,693,507.

The skilled artisan will recognize that any convenient element that is capable of initiating transcription in a plant cell plastid, also referred to as "plastid functional promoters", can be employed in the constructs of the present invention. A number of plastid functional promoters are available in the art for use in the constructs and methods of the present invention. Such promoters include, but are not limited to the promoter of the D1 thylakoid membrane protein, psbA (Staub et al. (1993) *EMBO Journal*, 12(2) :601–606), and the 16S rRNA promoter region, Prrn (Staub et al. (1992) *Plant Cell* 4:39–45). The expression cassette(s) can include additional elements for expression of the protein, such as transcriptional and translational enhancers, ribosome binding sites, and the like.

Regulatory transcript termination regions may be provided in the expression constructs of this invention as well. Transcript termination regions may be provided by any convenient transcription termination region derived from a gene source, for example, the transcript termination region that is naturally associated with the transcript initiation region. The skilled artisan will recognize that any convenient transcript termination region that is capable of terminating transcription in a plant cell may be employed in the constructs of the present invention.

In connection with the methods employing the use of a plastid lethal compound, any nucleic acid sequence providing tolerance to a plastid lethal compound may be used in the constructs for use in the methods of the present invention. Such genes include, but are not limited to, those genes that provide tolerance to herbicides. Such genes are known in the art, and include, but are not limited to, those providing tolerance to the herbicides glyphosate, bromoxynil or imidazolinone. Such genes have been reported by Stalker et al. (*J. Biol. Chem.* (1985) 260:4724–4728; glyphosate resistant EPSP, see also U.S. Pat. Nos. 5,633,435, and 5,804,425, and 5,627,061, herein incorporated by reference in their entirety), Stalker et al. (*J. Biol. Chem.* (1985) 263:6310–6314; bromoxynil resistant nitrilase gene), and Sathasivan et al. (*Nucl. Acids Res.* (1990) 18:2188; AHAS imidazolinone resistance gene).

The expression cassettes for use in the methods of the present invention also preferably contain additional nucleic acid sequences providing for the integration into the host plant cell plastid genome or for autonomous replication of the construct in the host plant cell plastid. Preferably, the plastid expression constructs contain regions of homology for integration into the host plant cell plastid. The regions of homology employed can target the constructs for integration into any region of the plastid genome, preferably the regions of homology employed target the construct to either the inverted repeat region of the plastid genome or the large single copy region. Where more than one construct is to be used in the methods, the constructs can employ the use of the regions of homology to target the insertion of the construct into the same or different position of the plastid genome.

Additional expression cassettes can comprise any nucleic acid to be introduced into a host cell plastid by the methods encompassed by the present invention including, for example, DNA sequences or genes from another species, or even genes or sequences that originate with or are present in the same species but are incorporated into recipient cells by genetic engineering methods rather than classical reproduction or breeding techniques. An introduced piece of DNA can be referred to as exogenous DNA. Exogenous as used herein is intended to refer to any gene or DNA segment that is introduced into a recipient cell, regardless of whether a similar gene may already be present in such a cell. The type of DNA included in the exogenous DNA can include DNA that is already present in the plant cell, DNA from another plant, DNA from a different organism, or a DNA generated externally, such as a DNA sequence containing an antisense message of a gene, or a DNA sequence encoding a synthetic or modified version of a gene.

Any method known for transforming plant cell plastids of the present invention may be employed as long as the resulting plant cells contain a population of plastids into which have been introduced a recombinant nucleic acid expressin construct having a DNA sequence encoding for a protein that provides tolerance to a plastid lethal compound or a plastid non-lethal compound as the case may be. Such methods include, but are not limited to, particle bombardment, PEG mediated transformation, and Agrobacterium-mediated transformation. Stable transformation of tobacco plastid genomes by particle bombardment has been reported (Svab et al. (1990) *Proc. Natl. Acad. Sci. USA* 87:8526–8530; Svab and Maliga (1993) *Proc. Natl. Acad. Sci. USA* 90:913–917). PEG mediated transformation of plastids is described by Koffer et al. (1998) in *Vitro Cell. Biol.-Plant,* 34:303–309, and Agrobacterium mediated plastid transformation is described by De Block et al. (1985) *EMBO Journal,* 4:1367–1372. Other methods for introducing recombinant constructs into plant cell plastids are known in the art, and are described for example in Svab et al. (1990) *Proc Natl. Acad. Sci. USA* 87:8526–8530, Sikdar et al. (1998) *Plant Cell Reports* 18:20–24, PCT Publication WO 97/2977, and Sidorov et al. (1999) *Plant J.* 19(2):209–216. Additional methods for introducing two constructs into a plant cell plastid are described for example in Carrer et al. (1995) *Bio/technology* 13:791–794. The methods described in the above references may be employed to obtain plant cells transformed with the plastid transformation constructs described herein.

The regeneration of whole plants from a transformed cell contained in the tissue used in transformation involves several growth stages. Typically, a tissue, having been excised from an adult plant or germinated seedling, is placed in a chemically defined medium under sterile conditions. By growing the explant under such controlled conditions for a period of time, an undifferentiated mass of cells, referred to as a callus, may form. By culturing this callus under the proper set of conditions, e.g., nutrients, light, temperature, humidity, and by providing the proper combination and concentration of plant growth regulators, the calli may be induced to form differentiated cells and regenerate plant shoots. Plant shoots, sometimes referred to as plantlets, containing meristem tissue are then transferred to a media for the induction of root production.

The selective media used and described herein may be liquid or solid, such as by the addition of a solidifying agent, such as agar. Liquid selective media allows for greater surface area of contact of the plant tissue with the selective media containing particular hormones, particular selective agents and other substances necessary to obtain regeneration.

The invention now being generally described, it will be more readily understood by reference to the following examples which are included for purposes of illustration only and are not intended to limit the present invention.

EXAMPLES

Example 1

Electron Microscopic Analysis of Tobacco Leaf Tissue Exposed to Glyphosate

Wild-type plants of *Nicotiana tabacum* cv Petit Havana were propagated in sterile hormone free MS medium (Murashige and Skoog (1962) *Physiol. Plant.* 15,473–497) supplemented with B5 vitamins in Phytatrays or sundae cups with a 16-hour photoperiod at 24° C. Leaf sections were aseptically removed and placed into new plant regeneration medium containing various concentrations of glyphosate, spectinomycin and phosphinothricin. The leaf material was collected at 1-week and 4-week time points and prepared for electron microscopic observation of plastid ultrastructure. As a control, wild-type leaf sections were exposed to the initially plastid non-lethal antibiotic, spectinomycin, under identical conditions, or to medium without any drug.

Cultured tobacco leaf pieces 1 mm$^2$ were fixed in 4% glutaraldehyde in 0.1 M sodium cacodylate buffer, pH 7.2 for 3 hours, with the first 30 minutes under vacuum. The tissue was further fixed in 1% osmium tetroxide in the above buffer for 90 minutes and stained with 1% aqueous uranyl acetate for 2 hours. Ethanol and propylene oxide were used to dehydrate the tissue prior to infiltration with a 1:1 mixture of Spurr's:EMbed 812 resin. The resin was polymerized at 60° C. for 48 hours. The resulting blocks were sectioned on a Leica Ultracut E microtome. Sections 80 nm thick were picked up on formvar/carbon-coated copper slot grids. The grids were stained with uranyl acetate and lead citrate in a LKB Ultrastainer and examined with a JEOL 1200 transmission electron microscope. All reagents were obtained from Electron Microscopy Sciences, Fort Washington, Pa.

Figure 1:
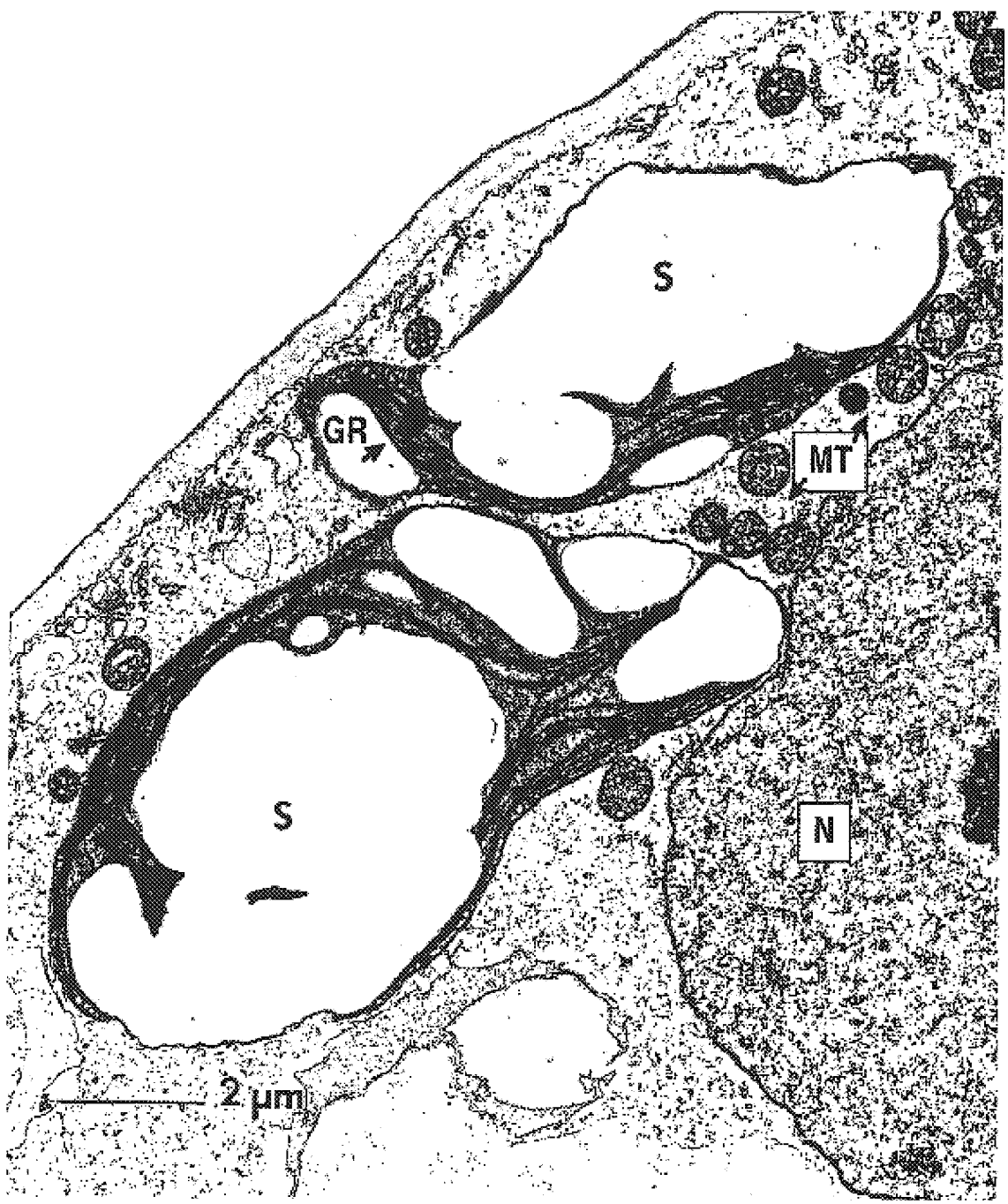
FIG. 1 provides transmission electron micrographs of thin sections of tissue from wild-type control plants cultured one week without drug treatment showing typical morphology of metabolically active photosynthetic plastids. Highly reticulate internal membrane structure of thylakoids (T) is seen including numerous regions of stacked grana (GR). The bulk of the plastid volume is filled with starch (S). The outer membrane of the plastid is clearly defined. The remainder of the plant cell shows numerous mitochondria (MT), and the nucleus (N) is rich in ribosomes.

Thin sections of tissue from wild-type control plants cultured one week without drug treatment show typical morphology of metabolically active photosynthetic plastids (FIG. 1). Highly reticulate internal membrane structure of thylakoids (T) is seen including numerous regions of stacked grana (GR). The bulk of the plastid volume is filled with starch (S). The outer membrane of the plastid is clearly defined. The remainder of the plant cell shows numerous mitochondria (MT) and the nucleus (N) is rich in ribosomes.

Figure 2:
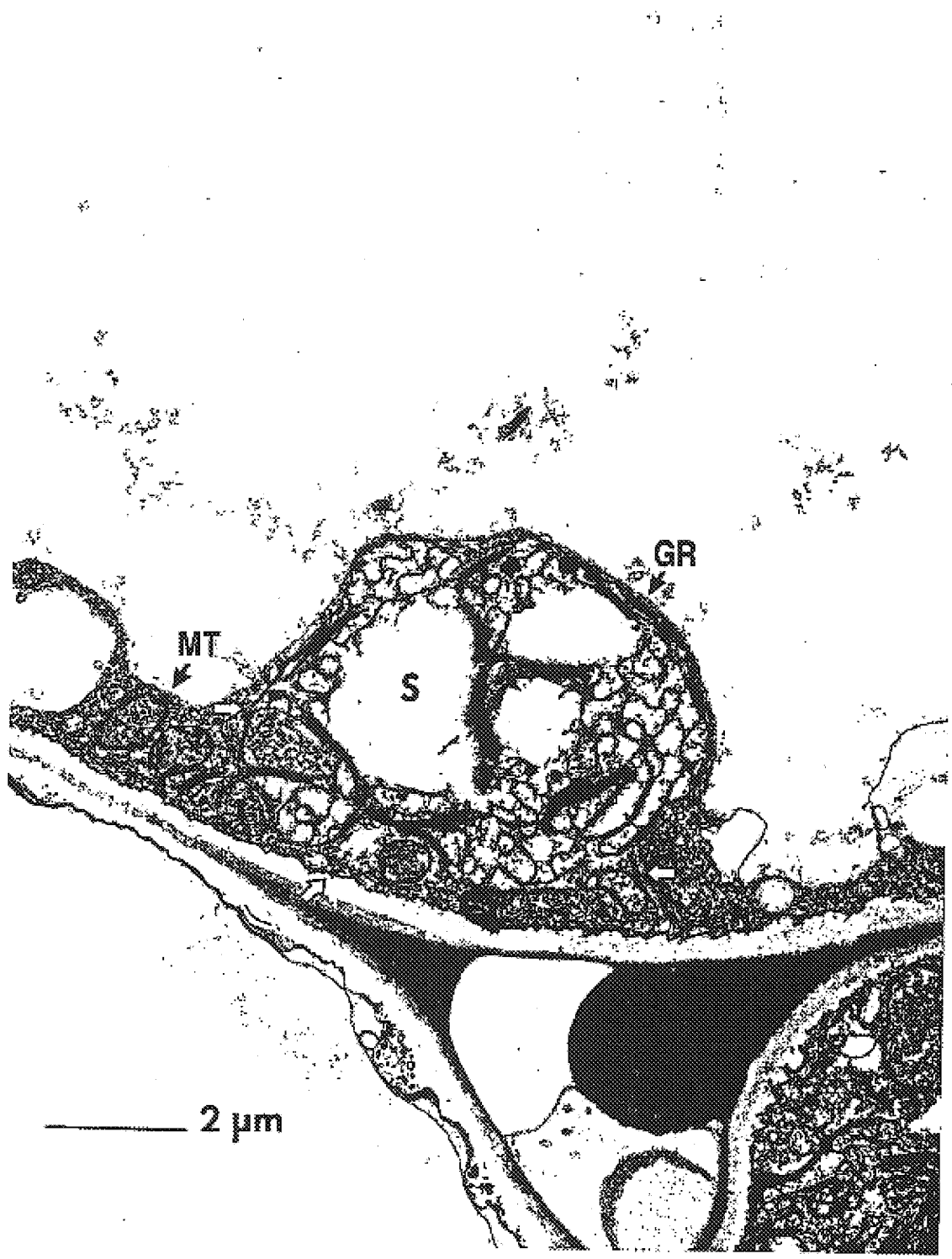
FIG. 2 provides transmission electron micrographs of tissues obtained from plants treated for one week with 50 μM glyphosate showing that the reticulate network of thylakoid membranes has disappeared, remnants of internal membranes are scattered throughout the stromal compartment, and only a few grana (GR) stacks remain, indicating a disintegration of the photosynthetic membranes. Starch (S) is much less abundant. The outer plastid membrane has also begun to degrade in several places (white arrow) and stromal contents are seen to overflow into the cell cytoplasm. Mitochondria (MT) are still visible.

Tissues obtained from plants treated for one week with 50 $\mu$M glyphosate show that the reticulate network of thylakoid membranes has disappeared, remnants of internal membranes are scattered throughout the stromal compartment and only a few grana (GR) stacks remain, indicating a disintegration of the photosynthetic membranes (FIG. 2). Starch (S) is much less abundant. The outer plastid membrane has also begun to degrade in several places (white arrow) and stromal contents are seen to overflow into the cell cytoplasm. Mitochondria (MT) are still visible.

Figure 3:
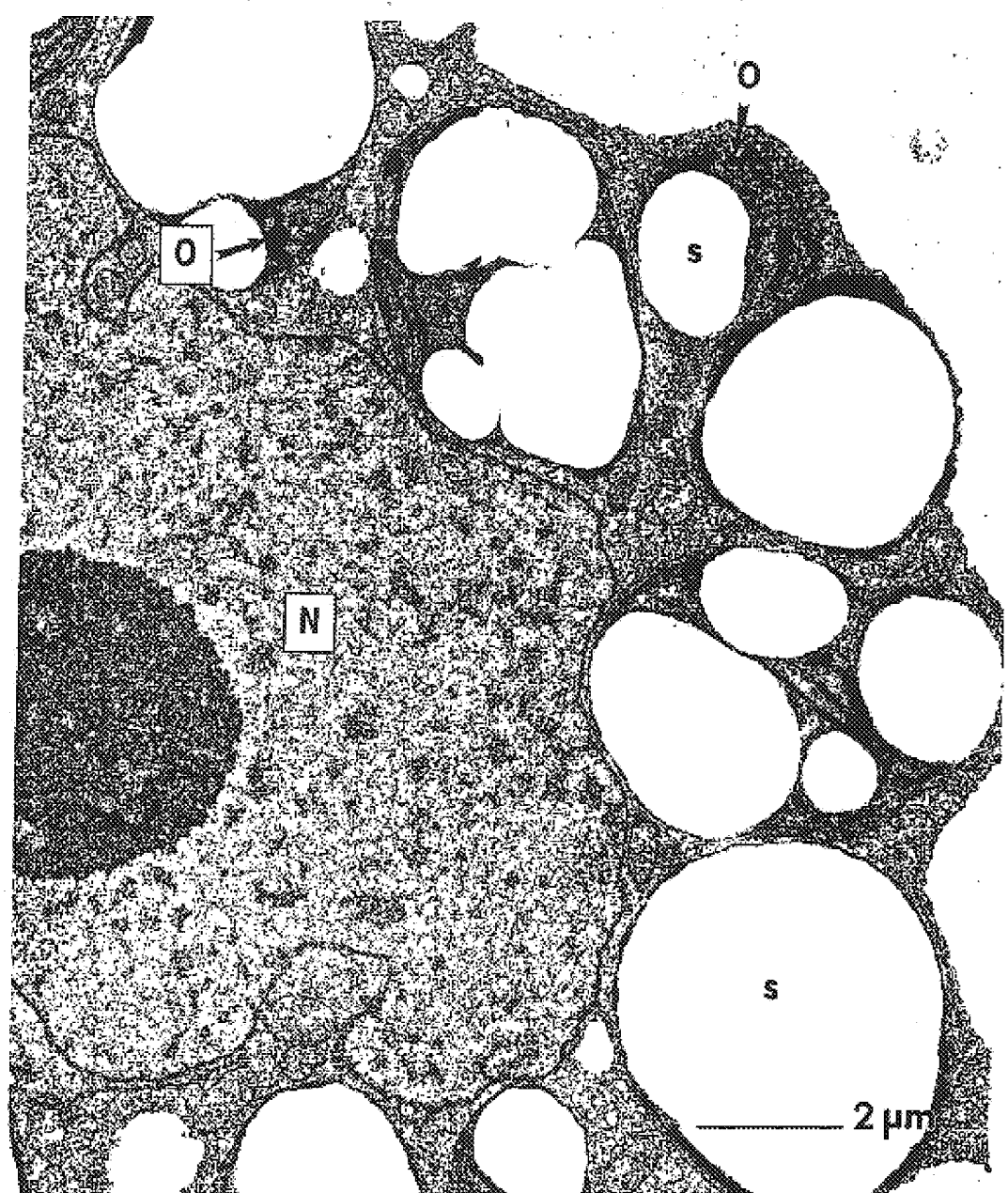
FIG. 3 provides transmission electron micrographs of tissues obtained from plants treated for four weeks with 50 μM glyphosate showing that the plastids appear to have recovered or adapted to some degree from the one-week time period. Although internal thylakoid membranes and grana are rare, starch has accumulated to fill a large volume of the plastid. Oil bodies (O) are present in most plastids, indicating sequestering of toxic metabolic breakdown products. Outer plastid membranes appear intact.

Tissues obtained from plants treated for four weeks with 50 µM glyphosate show that the plastids appear to have recovered or adapted to some degree (FIG. 3). Although internal thylakoid membranes and grana are rare, starch has accumulated to fill a large volume of the plastid. Oil bodies (O) are present in most plastids, indicating sequestering of toxic metabolic breakdown products. Outer plastid membranes appear intact.

Figure 4:
FIG. 4 provides transmission electron micrographs of tissues obtained from plants treated for one week with 200 μM glyphosate showing that the damage to plastid structure is occurring rapidly. Rare thylakoid membranes and grana are still observed, along with partially degraded membrane structures. Starch is nearly absent. Large numbers of oil bodies (O) are present. Outer membrane disintegration (white arrows) in multiple places is observed. The size of the plastids appears larger than in previous treatments relative to the nucleus (N).

Tissues obtained from plants treated for one week with 200 µM glyphosate show that the damage to plastid structure is occurring rapidly (FIG. 4). Rare thylakoid membranes and grana are still observed, along with partially degraded membrane structures. Starch is nearly absent. Large numbers of oil bodies (O) are present. Outer membrane disintegration (white arrows) in multiple places is observed. The size of the plastids appears larger than in previous treatments relative to the nucleus (N).

Figure 5:
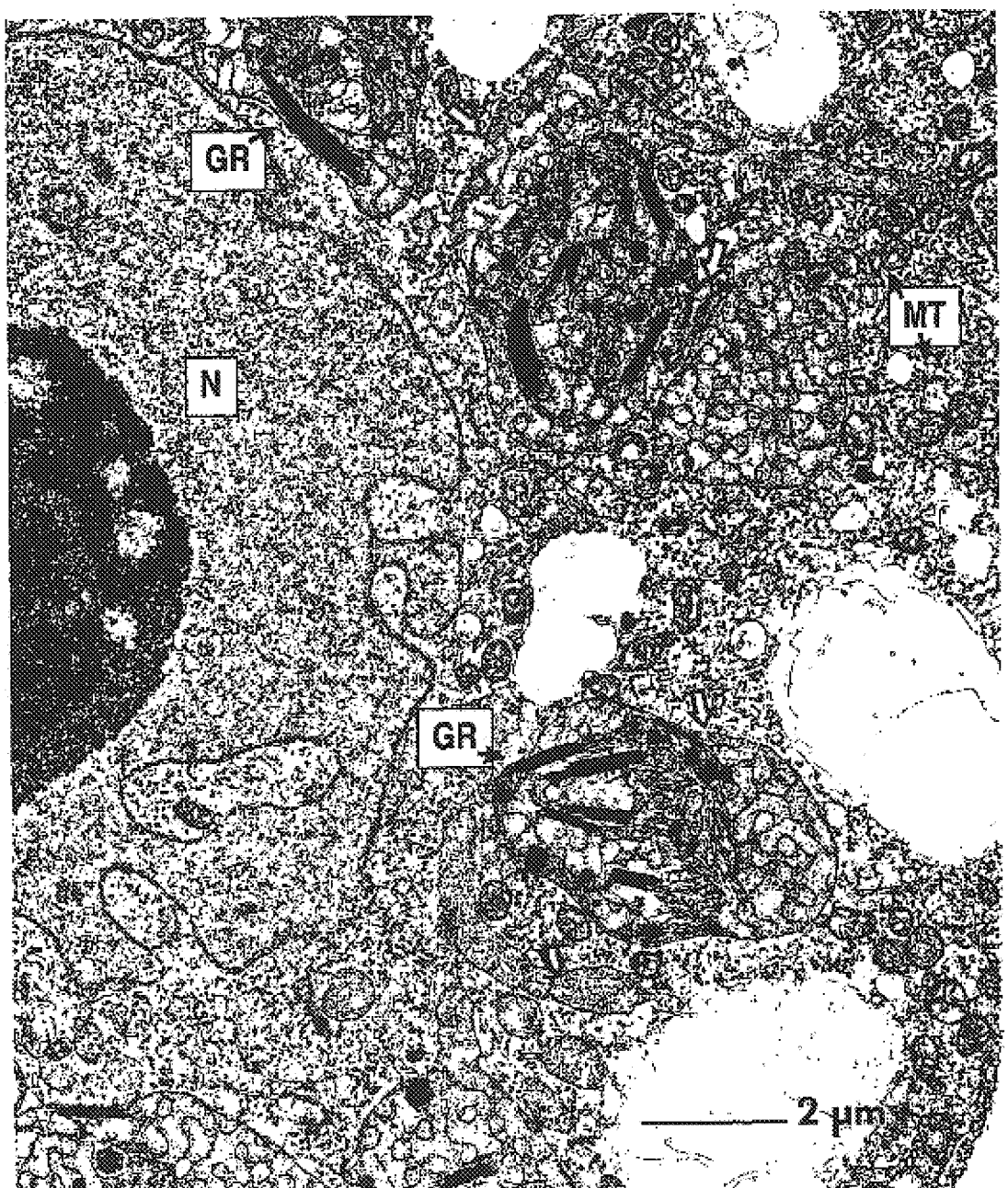
FIG. 5 provides transmission electron micrographs of tissues obtained from plants treated for four weeks with 200 μM glyphosate showing that some plastids appear to be recovering slightly whereas others are completely devoid of internal structure. Some grana are observed and some thylakoid membranes. No starch and no oil bodies are seen. Some outer membrane disintegration is observed (white arrows). A plastid with no internal structure is seen (*). The size of the plastid is small relative to the nucleus, indicating very little metabolic activity. Mitochondria are numerous.

Tissues obtained from plants treated for four weeks with 200 µM glyphosate are completely devoid of internal structure (FIG. 5); however, rare plastids are observed that appear to have some grana and some thylakoid membranes. No starch and no oil bodies are seen. Some outer membrane disintegration is observed (white arrows). A plastid with no internal structure is seen (*). The size of the plastid is small relative to the nucleus, indicating very little metabolic activity. Mitochondria are numerous.

Thus, glyphosate has minimal effect visually on plant cultures after 1 week. However, the plastid internal and outer membrane structure is clearly disintegrating, indicating lethality. After 4 weeks in culture at the lower concentrations, some glyphosate treated plant cultures actually begin to form shoot primordia indicating recovery of the tissue. However, the shoot primordia never elongate. The reason for this is unknown. It may be due to glyphosate degradation in the media or an unknown adaptation mechanism or a secondary auxin-like effect of glyphosate upon prolonged exposure.

Tobacco leaf tissue was also analyzed on medium containing lower concentrations of glyphosate. Tobacco tissue was cultured on TSO supplemented with 1 µM, 5 µM, 10 µM, or 20 µM glyphosate for 7 days. Cultured tissue was prepared for electron microscopy as described above.

Overall, the choroplasts are normal in structure at the 1 µM, 5 µM, and 10 µM concentrations. Tissues cultured on 20 µM glyphosate show increased damage to the thylakoid membrane system from 3 days to 7 days of exposure.

Figure 6:
FIG. 6 provides an electron micrograph picture of thin sections of tissue from plants cultured 7 days on medium supplemented with 1 μM glyphosate showing typical morphology of metabolically active photosynthetic plastids. The thylakoid membrane is intact and normal in appearance. The background stroma is smooth and of a normal density. Plastoglobuli are within the normal size range, approximately 0.25 μm in diameter. A large amount of starch is stored within the chloroplasts.

Thin sections of tissue from plants cultured 7 days on medium supplemented with 1 µM glyphosate show typical morphology of metabolically active photosynthetic plastids (FIG. 6). The thylakoid membrane is intact and normal in appearance. The background stroma is smooth and of a normal density. Plastoglobuli are within the normal size range, approximately 0.25 µm in diameter. A large amount of starch is stored within the chloroplasts.

Figure 7:
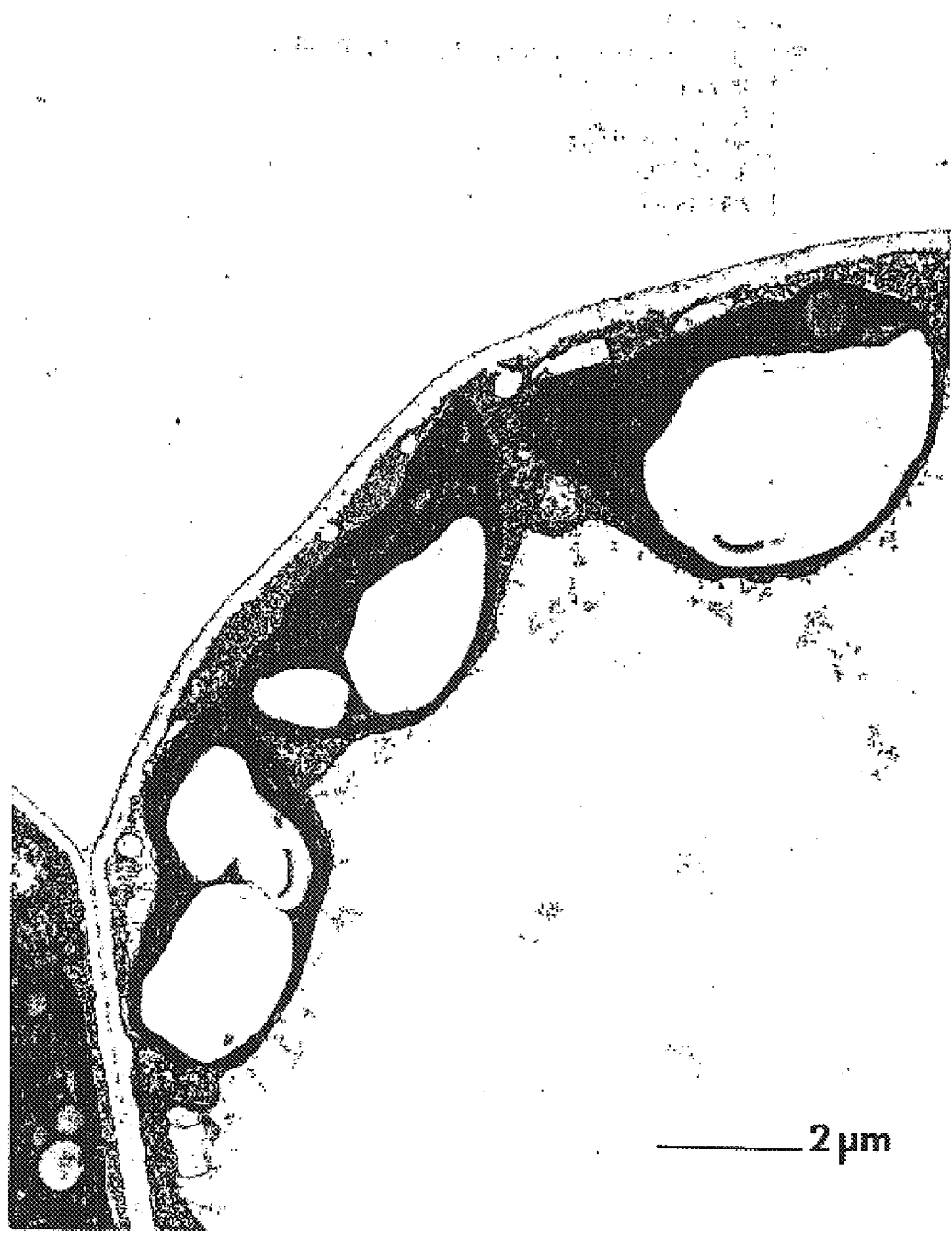
FIG. 7 provides an electron micrograph picture of thin sections of tissues obtained from plants treated for 7 days with 5 μM glyphosate showing a normal appearance.
Figure 8:
FIG. 8 provides an electron micrograph picture of thin sections of tissues obtained from plants treated for 7 days with 10 μM glyphosate showing a normal appearance.

Tissues obtained from plants treated for 7 days with 5 µM and 10 µM glyphosate are also normal in appearance similar to the tissue obtained from the 7 day 1 µM treatment. Electron micrographs of tissue thin sections of tissue treated for 7 days with 5 µM and 10 µM glyphosate are presented in FIGS. 7 and 8 respectively.

Figure 9:
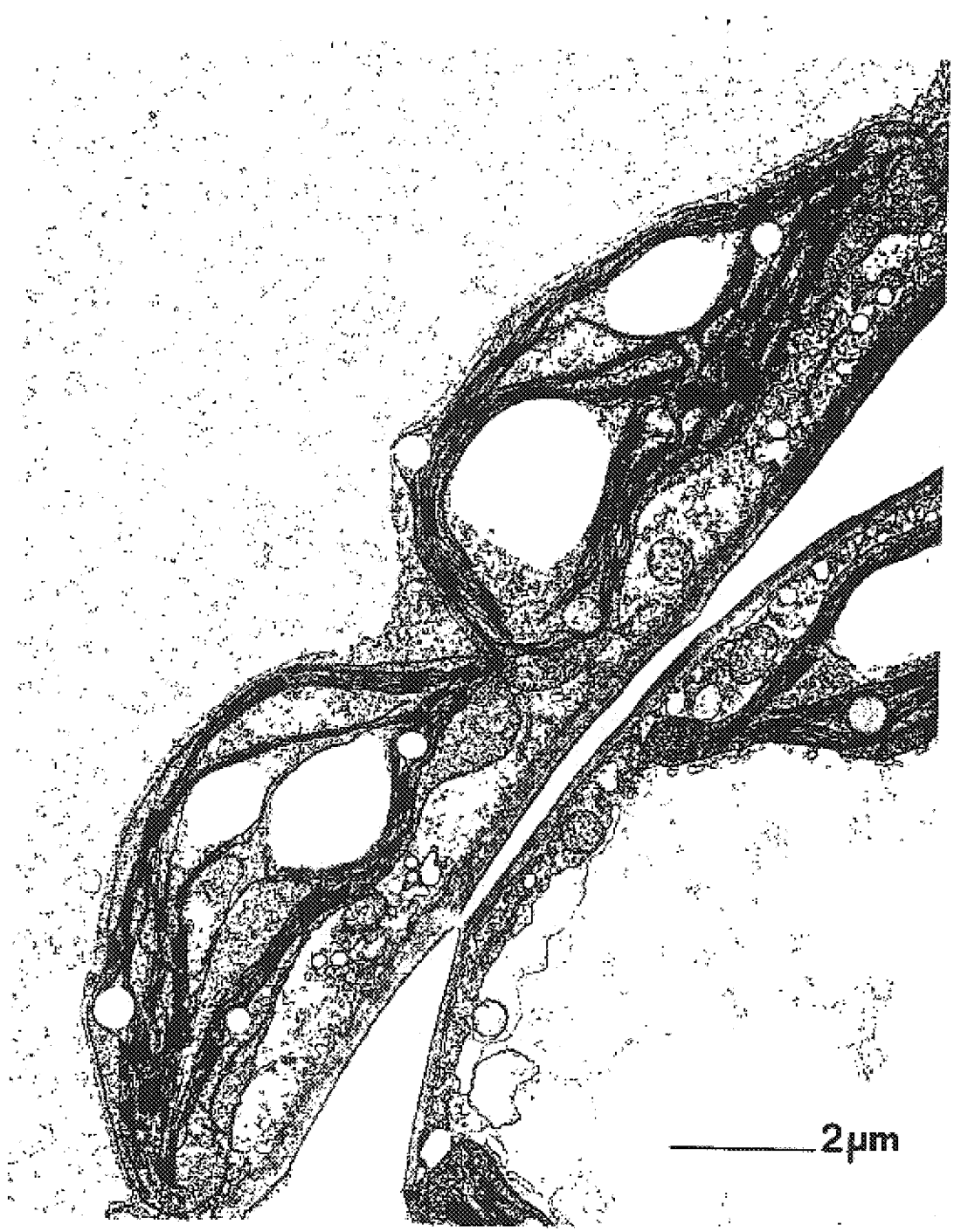
FIG. 9 provides an electron micrograph picture of thin sections of tissues obtained from plant tissue exposed to 20 μM glyphosate for 3 days shows that the chloroplasts are beginning to show morphological damage. The thylakoid membrane system is beginning to loose its stacked appearance and the stroma background is flocculent and less dense than at the 1 μM, 5 μM and 10 μM glyphosate concentrations.

Tissues obtained from plant tissue exposed to 20 µM glyphosate for 3 days show that the chloroplasts are beginning to show morphological damage (FIG. 9). The thylakoid membrane system is beginning to loose its stacked appearance and the stroma background is flocculent and less dense than at the 1 µM, 5 µM and 10 µM glyphosate concentrations.

Figure 10:
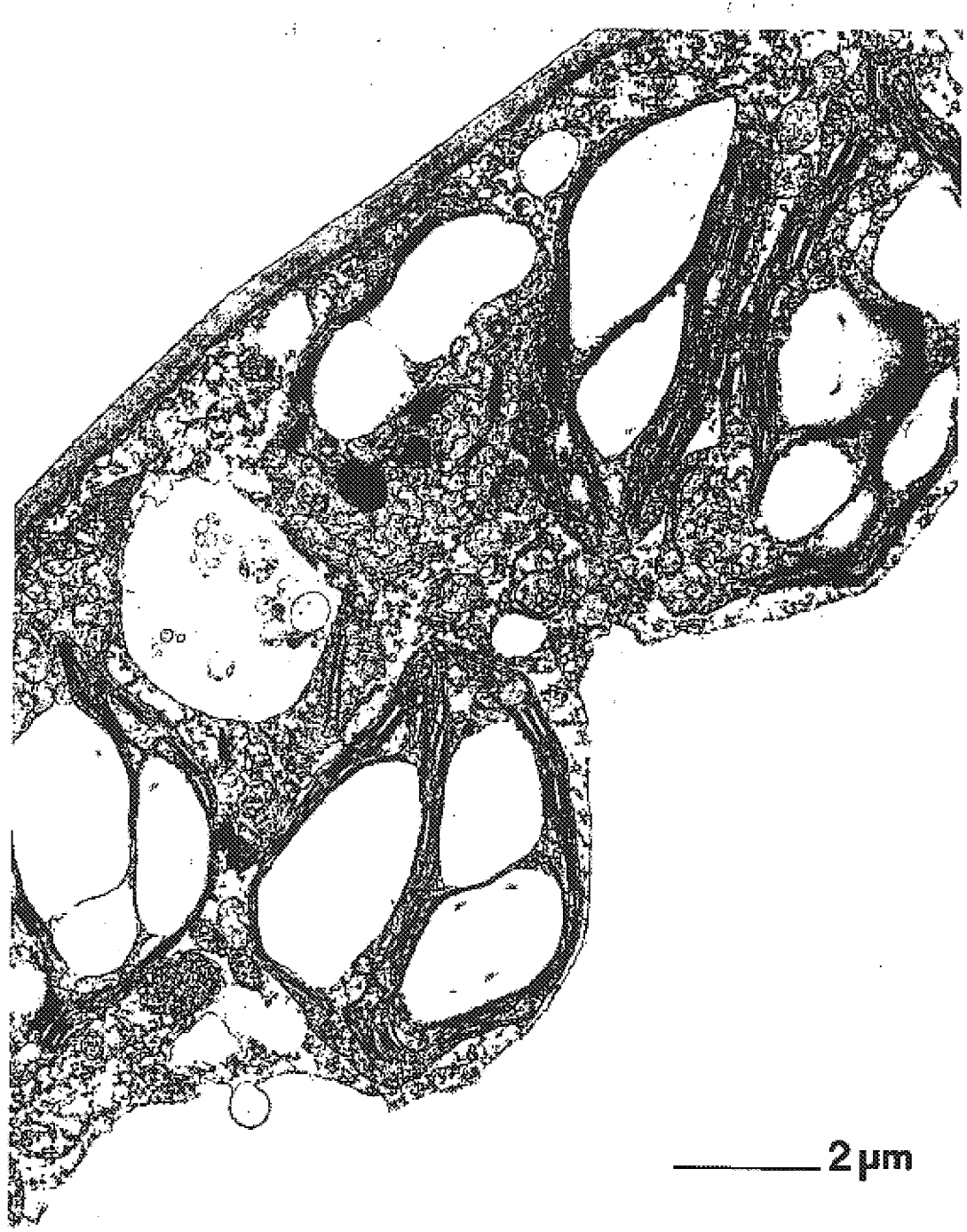
FIG. 10 provides an electron micrograph picture of thin sections of tissues obtained from plant tissue after 7 days of exposure to 20 μM glyphosate, showing the thylakoid membrane system is severely damaged, with the membrane stacks being completely unraveled in some cases and with noticeable gaps in others. The stroma is flocculent and has lost much of its density.

After 7 days of exposure to 20 µM glyphosate, electron microscopic observation shows that the thylakoid membrane system is severely damaged, with the membrane stacks being completely unraveled in some cases and with noticeable gaps in others (FIG. 10). The stroma is flocculent and has lost much of its density. Thus, lower concentrations of glyphosate demonstrate a sublethal effect on tobacco leaf tissues.

Tissues obtained from plants treated for one week with 500 mg/L spectinomycin show that the plastids look relatively normal (FIG. 11). Thylakoid membranes and grana are present, along with starch granules.

Figure 12A:
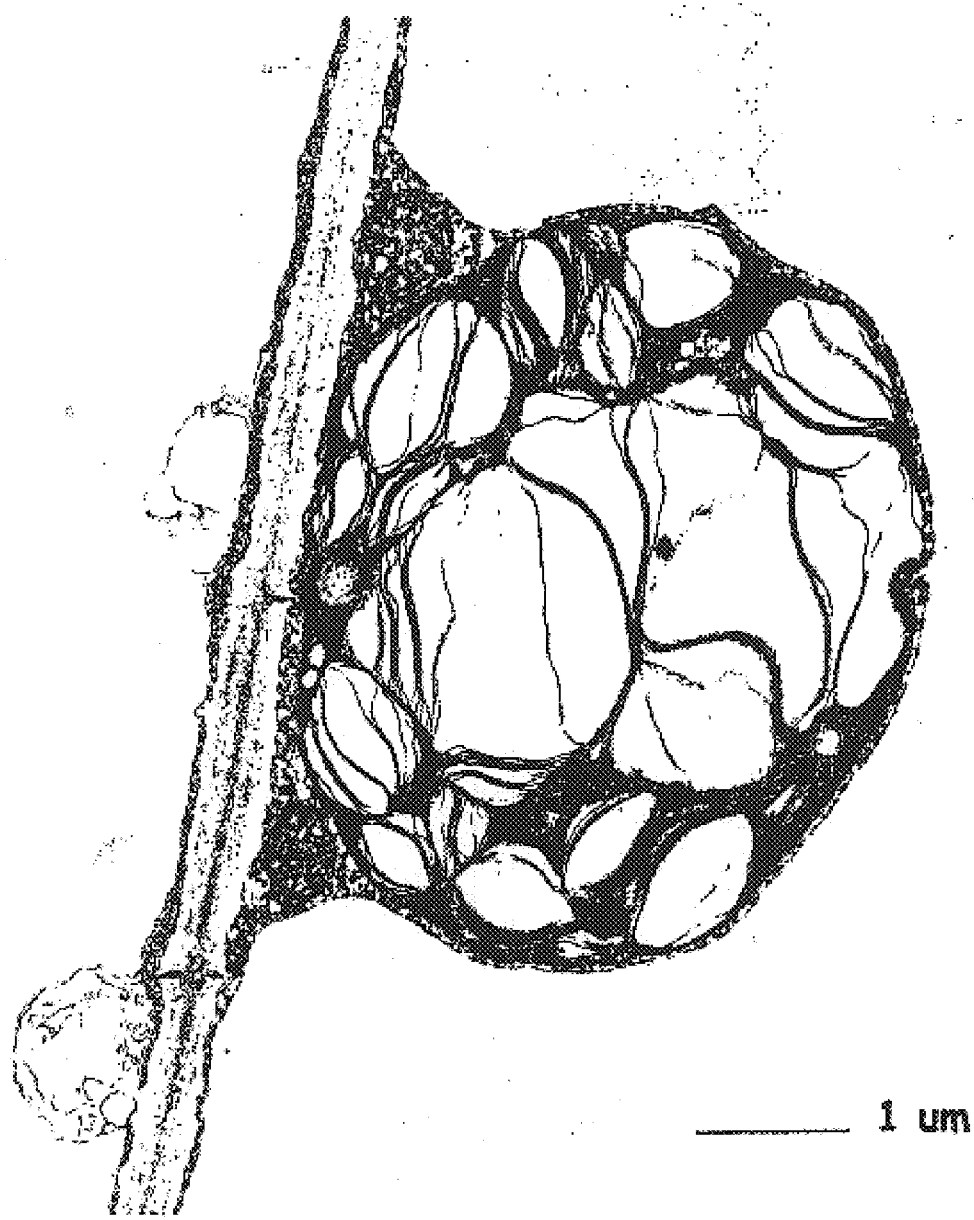
FIGS. 12A and 12B provide transmission electron micrographs of tissues obtained from plants treated for four weeks with 500 mg/L spectinomycin showing that the plastids internal membranes have broken down almost completely and become vacuolated, indicating lack or near lack of plastid photosynthetic function.
Figure 12B:

Tissues obtained from plants treated for four weeks with 500 mg/L spectinomycin show that the plastids internal membranes have broken down almost completely and become vacuolated, indicating lack or near lack of plastid photosynthetic function (FIGS. 12A and B).

Thus, plants cultured on medium containing spectinomycin for 1 week demonstrate that the spectinomycin had minimal effect on plant cultures visually and no apparent effect from the electron microscopic observations. However, after 4 weeks, when the tissue is completely bleached, the plastid internal membrane structure is destroyed.

To test the general effect of herbicides on plastid morphology, we examined tobacco leaf cultures that were grown in the presence of phosphinothricin (PPT, active ingredient in BASTA herbicide) at 4 mg/L, the concentration normally used for nuclear transformation. Leaves from healthy, tobacco plants at the same developmental stage were cut into about 5 mm×5 mm sections and placed on MS/B5 medium with 3% sucrose, 1 mg/L BAP, 0.1 mg/L NAA and 4 mg/L phosphinothricin for the 3, 7 or 12 days. The leaf sections were then fixed and processed for TEM analysis.

The results show that even at the earliest time point (3 days), PPT has a dramatic effect on plastid ultrastructure (FIG. 13). Thylakoid membranes are completely absent and the stromal contents are densely stained indicating a tight packing of accumulated toxic compounds. Starch is present, but less than in wild-type cells. The outer plastid membrane is also apparently missing in some places, and some membranous structures that are possibly thylakoid remnants are leaked into the cell cytosol. The effect at 7 days (FIG. 14) and 12 days (FIG. 15) is even more dramatic, with oil bodies accumulated in the organelles. Starch granules are very small and dispersed.

Example 2

Expression Construct Preparation

The vectors pZS 197 and pPRV 112 are as described by Svab et al. ((1993), *Proc. Natl. Acad. Sci. U.S.A.*, 90:913–917) and Zoubenko et al. ((1994) *Nucleic Acids Res.*, 22:3819–3824), respectively. The pZS197 construct directs the expression of the aadA selectable marker from the PrrnPEP promoter (recognized by the plastid-encoded polymerase) and the short ribosome binding site (rbs) region of the rbcL gene (rbcL(S)). This vector contains regions of homology for integration of the expression cassette into the single copy region of the tobacco plastid genome between the rbcL and accD sequences. The pPRV112 construct directs the expression of the aadA selectable marker from the same PrrnPEP promoter and rbcL(S) sequences and contains regions of homology for integration of the expression cassette into the repeat region of the tobacco plastid genome between the trnV and rps12/rps7 3' sequences.

Figure 18:
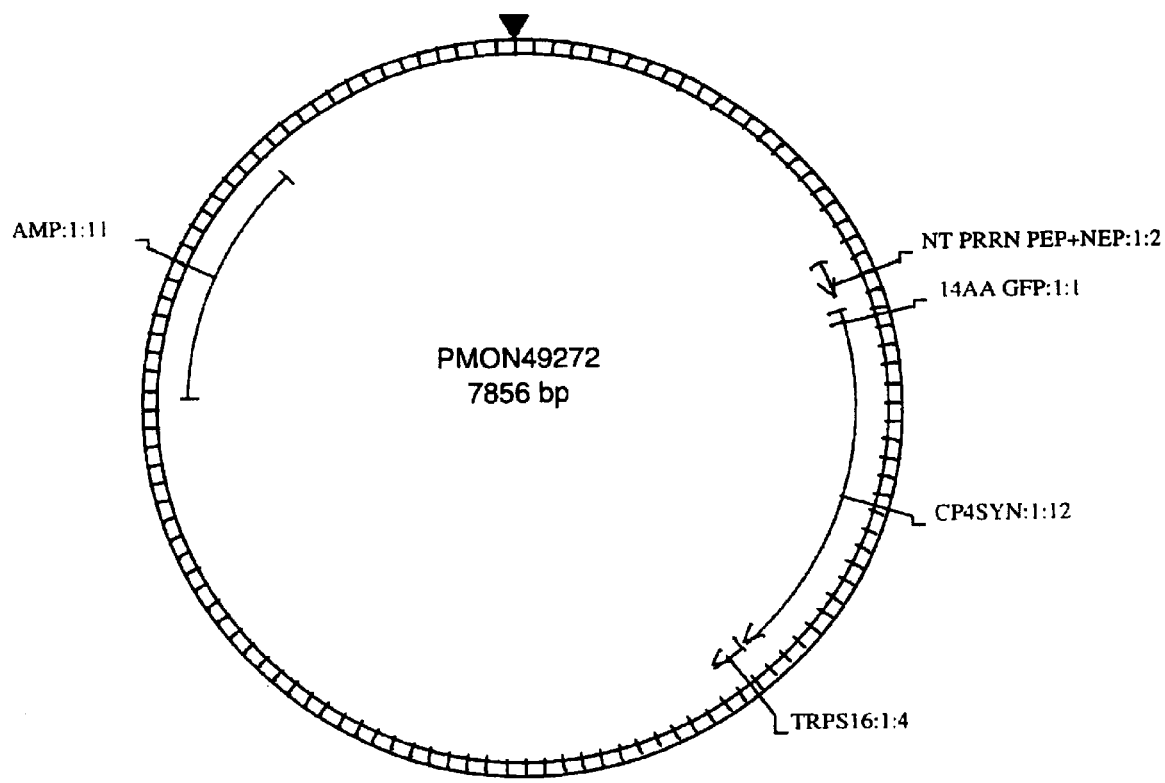
FIG. 18 is a plasmid map of pMON49272.
Figure 19:
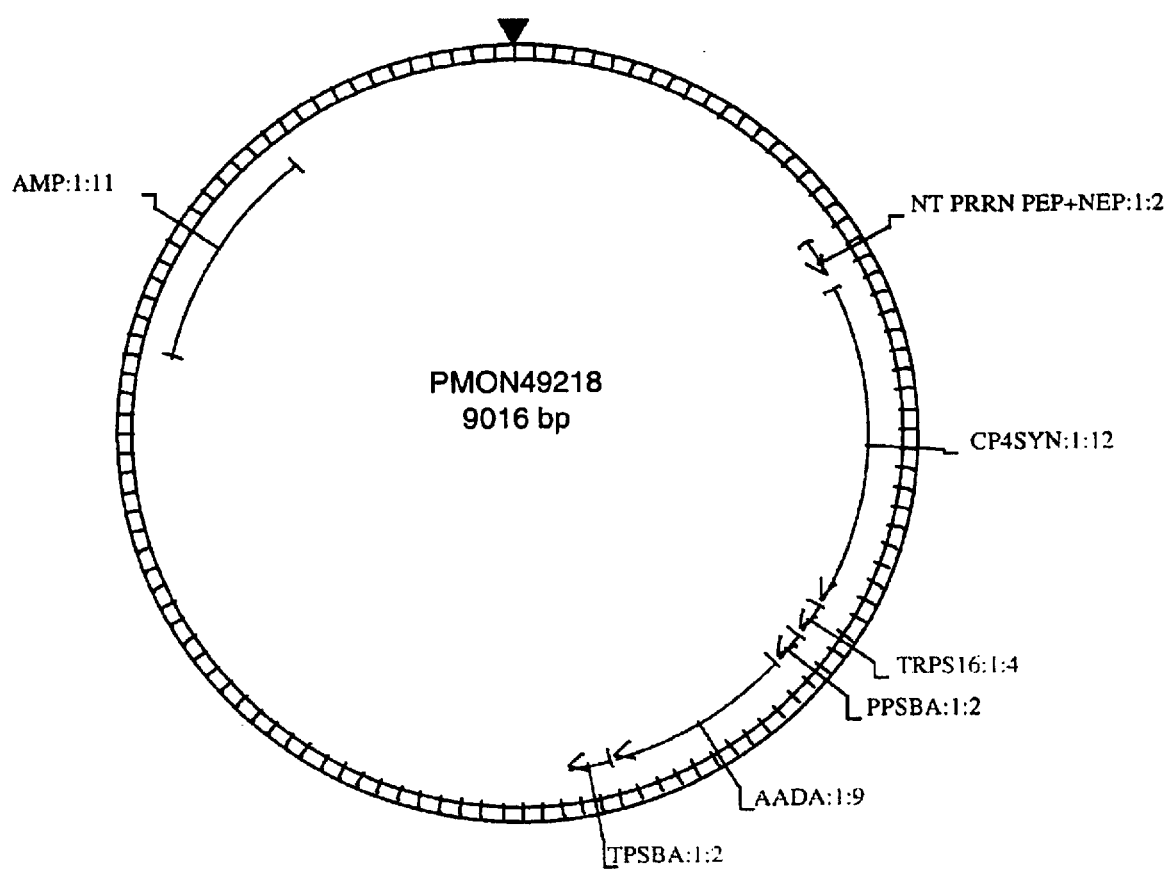
FIG. 19 is a plasmid map of pMON49218.

Two constructs are prepared to direct the expression of the synthetic CP4 EPSPS (U.S. Pat. Nos. 5,633,435, 5,804,425, and 5,627,061). Both constructs utilize the PrrnPEP promoter including the NEP regions (recognized by the nuclear-encoded polymerase) (SEQ ID NO: 1) and the rbs regions from the T7 bacteriophage gene 10 (G10L). The expression constructs also includes the DNA sequence encoding the first 14 amino acids of the Green Fluorescent Protein (GFP) operably linked to the 5' terminus of the CP4 coding sequence. The complete sequence of the PrrnPEP+NEP/G10L/14aaGFP fusion is provided in SEQ ID NO:2. These constructs also employ the use of the transcriptional termination region of the plastid gene rps16 sequence (Trps16). One construct, pMON49272 (FIG. 18), contains the PrrnPEP+NEP/G10L/14 aaGFP/synCP4/Trps16 cassette flanked by regions of homology for integration of the expression cassette into the repeat region of the tobacco plastid genome between the trnV and rps12/rps7 3' sequences. The second construct, pMON49218 (FIG. 19), contains the same expression cassette and is flanked by regions of homology for integration of the construct into the single copy region of the tobacco plastid genome between the rbcL and accD sequences.

Figure 20:
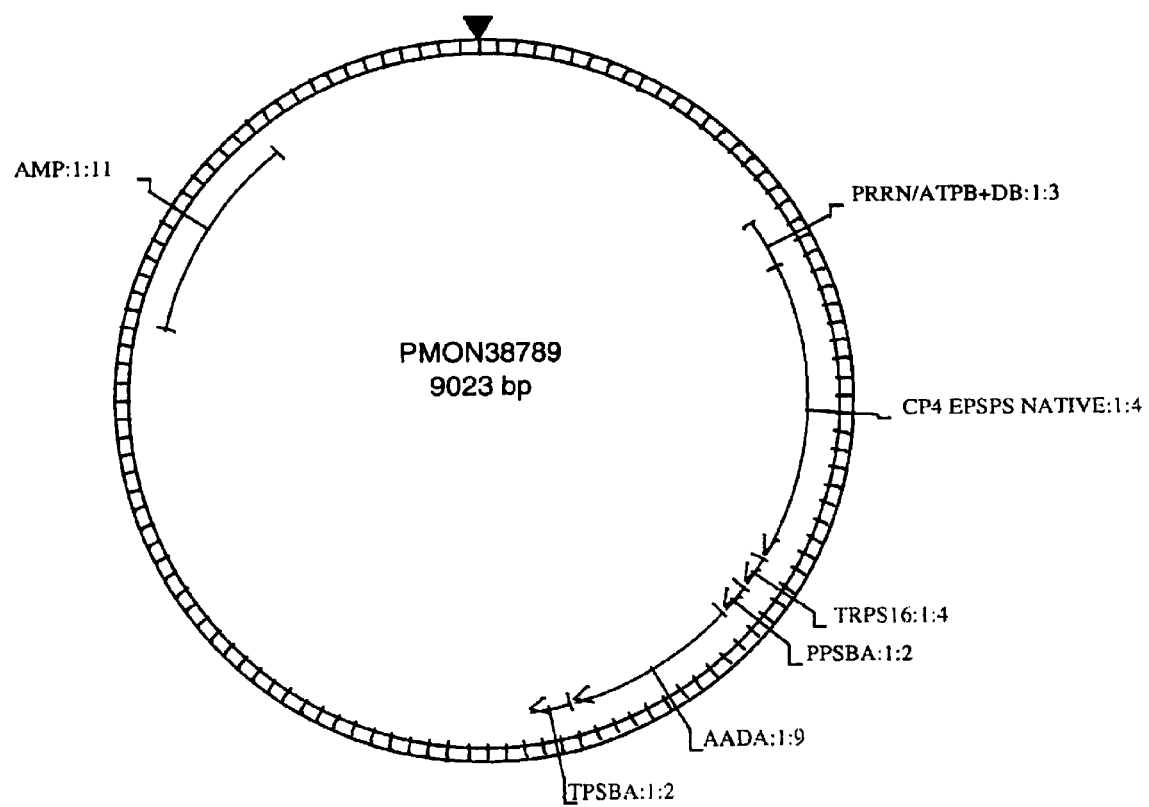
FIG. 20 is a plasmid map of pMON38789.

Another construct, pMON38789 (FIG. 20) was also prepared to express the synthetic CP4 sequence from the PrrnPEP promoter fused with the translational leader of the plastid atpB gene (atpBL) (Orozco et al. (1990) *Current Genetics*, 17:65–71). The synthetic CP4 sequence is operably linked at its 5' terminus to sequences encoding the first 14 amino acids of the atpB gene. The expression cassette also employs the transcriptional termination region Trps16. The expression cassette is flanked by regions of homology for integration into the tobacco plastid genome between the trnV and the rps12/rps7 3' sequences.

Figure 21:
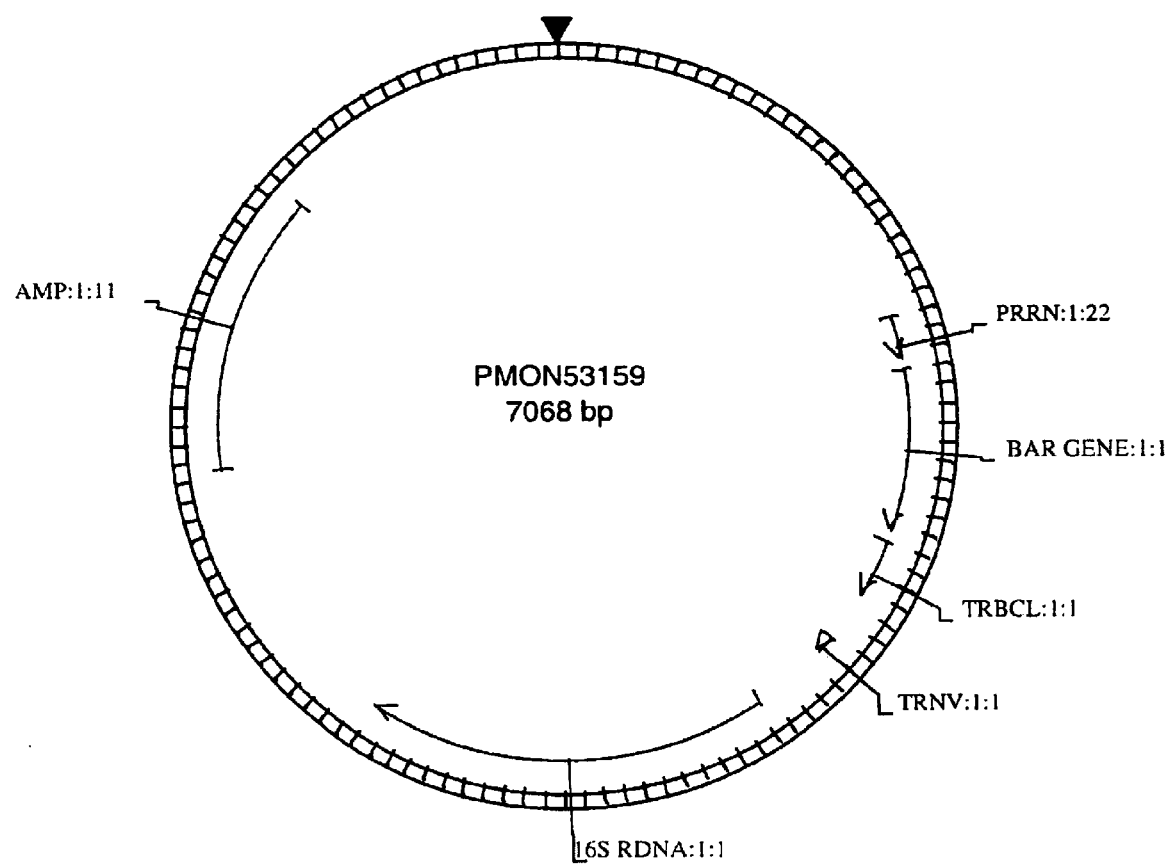
FIG. 21 is a plasmid map of pMON53159.

Additional constructs were prepared to direct the expression of the bar gene for phosphinothricin (PPT) resistance from the PrrnPEP promoter. pMON53159 (FIG. 21) contains the bar gene (DeBlock et al. (1987) *EMBO J.* 6:2513–2518) expressed from the PrrnPEP/rbcL(S) promoter and uses the rbcL transcriptional termination region (TrbcL). This construct also carries regions of homology to target integration of the expression cassette into the tobacco plastid genome between the trnV and rps12/rps7 3' sequences.

Example 3

"Two Phased" Selection of Plastid Transformants and Segregation of CP4 Containing Lineages.

Tobacco plastids are transformed by particle gun delivery of microprojectiles as described by Svab and Maliga (*Proc. Natl. Acad. Sci.* (1993) 90:913–917), and described here.

Dark green, round leaves are cut, preferably from the middle of the shoots, from 3–6 week old *Nicotiana tabacum* cv. Havana that have been maintained in vitro on hormone-free MS medium (Murashige and Skoog, (1962) *Physiol Plant.* 15, 473–497) supplemented with B5 vitamins in Phytatrays or sundae cups with a 16-hour photoperiod at 24° C. Each cut leaf is then placed adaxial side up on sterile filter paper over tobacco shoot regeneration medium (TSO medium: MS salts, 1 mg/L $N^6$-benzyladenine, 0.1 mg/L 1-naphthaleneacetic acid, 1 mg/L thiamine, 100 mg/L inositol, 7 g/L agar pH 5.8 and 30 g/L sucrose). Leaves are preferably placed in the center of the plate with as much contact with the medium as possible. The plates are preferably prepared immediately prior to use but may be prepared up to a day before transformation by particle bombardment by wrapping in plastic bags and storing at 24° C. overnight.

Tungsten or gold particles are sterilized for use as microcarriers in bombardment experiments. Particles (50 mg) are sterilized with 1 mL of 100% ethanol, and stored at −20° C. or −80° C. Immediately prior to use, particles are sedimented by centrifugation, washed with 2 to 3 washes of 1 mL sterile deionized distilled water, vortexed and centrifuged between each wash. Washed particles are resuspended in 500 µL 50% glycerol.

Sterilized particles are coated with a 1:1 mixture of two plasmid DNAs for transformation. Twenty-five micoliter aliquots of sterilized particles are added to a 1.5-mL microfuge tube, and 5 µg of DNA of interest is added and mix by tapping. Thirty-five microliters of a freshly prepared solution of 1.8 M $CaCl_2$ and 30 mM spermidine is added to the particle/DNA mixture, mixed gently, and incubated at room temperature for 20 minutes. The coated particles are sedimented by centrifuging briefly. The particles are washed twice by adding 200 µL 70% ethanol, mixing gently, and centifuging briefly. The coated particles are resuspended in 50 µL of 100% ethanol and mixed gently. Five to ten microliters of coated particles are used for each bombardment.

Transformation by particle bombardment is carried out using the PDS 1000 Helium gun (Bio Rad, Richmond, Calif.) using a modified protocol described by the manufacturer.

Plates containing the leaf samples are placed on the second shelf from the bottom of the vacuum chamber and bombarded using the 1100 p.s.i. rupture disk. After bombardment, petri plates containing the leaf samples are wrapped in plastic bags and incubated at 24° C. for 48 hours as a delay period prior to phase one culturing.

After the 48-hour delay, bombarded leaves are cut into approximately 0.5 $cm^2$ pieces and placed abaxial side up on phase-one selection medium on TSO medium supplemented with 500 µg/mL spectinomycin. After 4 to 8 weeks on this medium, small, green spectinomycin resistant shoots will appear on the leaf tissue. These shoots will continue to grow on spectinomycin containing medium and are referred to as primary putative transformants.

As soon as putative plastid transformants selected in "phase one" by spectinomycin resistance are identified, they are transferred for "phase two" selection on medium containing glyphosate. Transformants that show new shoot formation on glyphosate medium are considered positive for the "phased selection" and were therefore co-transformed with both the aadA-containing and the CP4-containing plasmids. Independent shoots that arise on glyphosate medium are termed subclones. If available, multiple subclones for each independent line are assayed by Southern blot analysis. The analysis is designed to determine if the CP4 and/or aadA genes are present on the same or different plastid genomes. Lines carrying CP4 on different genomes are referred to as "CP4+ segregants".

If desired, primary putative transformants arising in phase one selection can also be screened for resistance to streptomycin, to confirm that these are not spontaneous spectinomycin resistant shoots. Small pieces of leaf from the primary transformants (approximately 0.5 cm$^2$) are cut and placed abaxial side up on TSO medium supplemented with 500 µg/mL each of spectinomycin and streptomycin. Positive transformants are identified as the shoots that form green callus on the TSO medium containing spectinomycin and streptomycin.

From the two phased experiment utilizing plasmids pZS197 and pMON49272 for transformation (Table 1) Southern blot hybridizations were performed to confirm transplastomic lines and to confirm that the plastid genomes contain the CP4 plastid construct providing resistance to the plastid lethal compound glyphosate. As shown in the Southern blot in FIG. 16B, integration of aadA into the LSC region would produce a 4.3 kb transplastomic band (TR1). Line 48-1 carries only wild-type (3.0 kb, WT1) DNA in this region, indicating that the aadA gene has segregated away from the glyphosate resistance gene in this line. On the other hand, probing for the CP4 gene in the IR region as shown in FIG. 16C produced only the transplastomic 4.1 kb and 0.9 kb bands (TR2) and no detectable wild-type 3.3 kb (WT2) band. Therefore, line 48-1 is homoplasmic for CP4 and does not carry any aadA gene sequences and is therefore a CP4+ segregant. This result proves the utility of the "phased selection" approach.

Lines 9-2-2 and line 9-2-3 are heteroplasmic for the integration of the aadA gene and carry more wild-type genomes (3.0 kb) than aadA-containing genomes (4.3 kb). However, these lines are nearly homoplasmic for integration of the CP4 gene (4.1 and 0.9 kb bands). This indicates that at least 3 different populations of genomes are present in these lines: wild-type, aadA-containing genomes (either with or without CP4), and genomes carrying CP4 alone. Genomes carrying CP4 alone were recovered after shoot regeneration on another round of culturing on glyphosate containing medium. These lines, therefore, represent additional CP4+ segregant lines. The results of the Southern blot hybridizations are presented in FIG. 16.

Other lines, including 4-1-1, 4-1-2, 9-1-1, 9-1-2, 9-1-3, and 9-2-1, contain equal proportions of both aadA-containing and CP4-containing genomes indicating that these are co-transformed onto the same genome. The results of the Southern blot hybridizations are presented in FIG. 16.

The data for the transformation experiment are summarized in Table 1 below.

TABLE 1

| Vectors | #spec resistant | #glyphosate resistant | #CP4+ SEGREGANTS |
|---|---|---|---|
| pZS197 + pMON49272 | 52 | 10 | 5 |

This data indicates a frequency of aadA+CP4 cotransformation in phase 1 as 20%; in phase 2, half of these (50%) segregate genomes containing the CP4 gene alone (CP4+ segregants). Therefore, the overall frequency of segregated CP4+genomes is 10% of the total transformants using the phased selection scheme.

Segregation to homoplasmic genomes carrying only the CP4 gene has been achieved in multiple independent transformed lines. As an example, the original transformed 9-2-2 line was used for plant regeneration. Probing for aadA (FIG. 16B) shows only the wild-type DNA pattern in all subclones (9-2-2a, b, c, d), indicating loss of aadA. In contrast, probing for CP4 (FIG. 16C) shows only homoplasmy for the CP4 integration event in all subclones. Plants from this line were placed in the greenhouse to set seed. Seeds were collected and germinated on medium containing spectinomycin or medium containing glyphosate. As can be seen in Table 3, all of the seed progeny from this line that were tested on spectinomycin were sensitive proving loss of the aadA gene whereas all of the seed progeny tested were resistant to glyphosate proving segregation to homoplasmy and inheritance of the CP4 gene.

Figure 22:
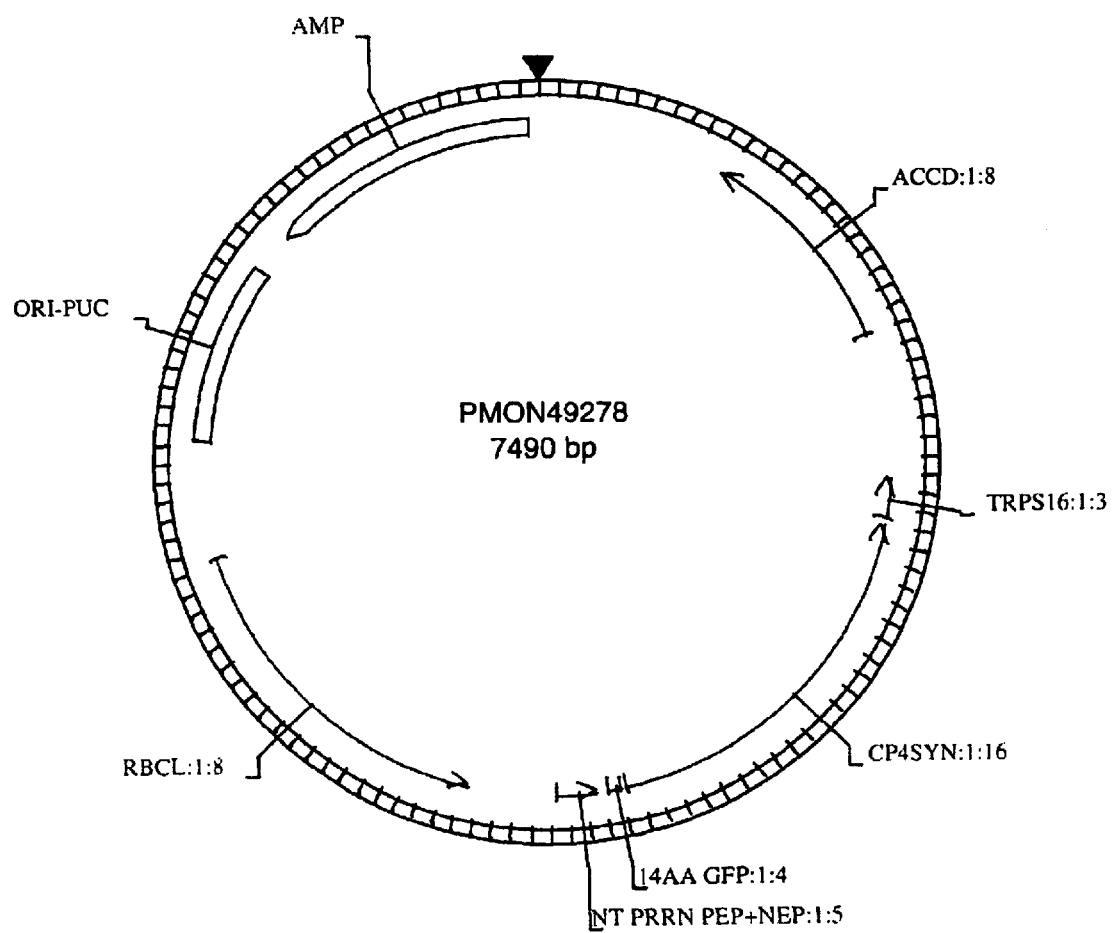
FIG. 22 is a plasmid map of pMON49278.

Transformation events from targeting aadA to the Inverted Repeat (IR) and CP4 to the Large Single Copy (LSC) region have been characterized and show results similar to above. For example, the experiment where aadA is targeted to the IR region (pPRV112) and the CP4 is targeted to the LSC region (pMON49278; FIG. 22) generated 6 glyphosate resistant lines after phase two selection. Three of these lines segregated CP4+ only in subsequent rounds of plant regeneration on medium containing glyphosate. Two clones from line 15-1-2 were moved to soil to allow seed set. Table 3 again shows that all of the seed progeny from these lines are uniformly sensitive to spectinomycin and resistant to glyphosate. This result indicates that the relative locations used for targeting the co-bombarded plasmids does not affect the ultimate segregation of glyphosate resistant CP4+ segregants.

Furthermore, transformation and segregation to CP4+has been achieved after targeting aadA and CP4 to the same (LSC) location. This latter result is novel, because although the overall number of glyphosate resistant lines is low, 100% of these segregate CP4. Table 2 below summarizes the above data.

TABLE 2

| TARGETS | # EXP | # SPEC$^R$ | # GLY$^R$ | % Co-Transformed | CP4+ Segregants | % Segregants |
|---|---|---|---|---|---|---|
| aadA (LSC)/ CP4 (IR) | 6 | 57 | 11 | 20 | 7 | 64 |
| aadA (IR)/ CP4 (LSC) | 1 | 28 | 6 | 21 | 3 | 50 |
| aadA (LSC)/ CP4 (LSC) | 1 | 29 | 1 | 3 | 1 | 100 |

TABLE 3

| Line # | # Seeds on Spec | % Resistant | # Seeds on Glyphosate | % Resistant |
|---|---|---|---|---|
| gy9915-1-2-3 | 800 | 0 | 688 | 100 |
| gy9915-1-2-2 | 1536 | 0 | 1040 | 100 |
| gy9909-2-2-2b | 496 | 0 | 504 | 100 |

Selfed seeds from each line were sterilized and plated on medium containing either 500 mg/L spectinomycin or 50 µM glyphosate. The results were scored 12 days after plating.

Phosphinothricin Selection

Direct selection of phosphinothricin (PPT) resistant transformants on lethal levels of PPT using plasmid pMON53159 carrying the bar gene alone were unsuccessful. Cultures that were directly selected in this way (4 mg/L phosphinothricin, PPT) resulted in explants that were bleached and demonstrated little or no cell expansion. No regenerants were obtained from the 60 plates bombarded.

The phased selection approach was then attempted using a combination of plasmids pMON53159 and pZS197, carrying the bar gene for resistance to PPT and the aadA gene for resistance to spectinomycin, respectively. Bombarded leaves were selected on spectinomycin in phase one and on 2 or 4 mg/L phosphinothricin in phase two.

From the 60 plates bombarded, 32 spectinomycin resistant shoots were identified. Of the 32 shoots, 12 were shown to be resistant to streptomycin, indicating that they are true plastid transformants whereas the others were spontaneous spectinomycin resistant mutants. The 12 transformed shoots were then transferred for "phase two" selection of the bar gene on medium containing 2 or 4 mg/L PPT. Primary transformants that showed new shoot formation on PPT medium were considered positive for the "phased selection" and were therefore co-transformed with both the aadA-containing and the bar-containing plasmids. One of the 12 transformed shoots was shown to be resistant to phosphinothricin when grown on 2 mg/L PPT. Results from culturing on 4 mg/L PPT medium were unclear due to slow growth on this medium. Independent shoots that arise on PPT medium are termed subclones. Four subclones for this line were assayed by Southern blot analysis. The analysis was designed to determine if the bar and/or aadA genes are present on the same or different plastid genomes. Lines carrying bar and aadA on different genomes are referred to as "bar+ segregants". While one of the subclones carried aadA and bar on the same genomes, three independent subclones did not carry aadA and were homoplasmic for bar only. Therefore, three bar+ segregants were obtained from this experiment. Results of the selection are provided in Table 4 below. The Southern blot analysis of these three bar+segregants is shown in FIGS. 16D, E. All three lines (20-1-1, 20-1-2 and 20-1-4) have lost the aadA gene as evidenced by the wild-type pattern (WT3) after probing the aadA region. In contrast, probing of the bar region shows that all lines carry the 3.7 kb TR3 hybridization pattern. Subclones from each line are homoplasmic for bar, indeed confirming that these are bar+segregants.

TABLE 4

| Constructs | # Plates Shot | Selection | # Plants Spec$^R$ | # Plant PPT$^R$ |
|---|---|---|---|---|
| pMON53159 | 60 | 4 mg/L PPT | — | 0 |
| pMON53159 + pZS197 | 60 | Spec 500 mg/L then 2 mg/L PPT or 4 mg/L PPT | 12 | 1 |

Low percentage of lines identified as PPT resistant after phase two selection may be due to severe lethality of PPT or the need to amplify the bar gene to a higher level before phase two selection.

Example 4

Direct Selection of Plastid Transformed Cells on Glyphosate

Sixty tobacco leaves were prepared and bombarded with the plastid expression construct pMON38789 as described in Example 3. After bombardment, plates containing the transformed tobacco leaves were incubated on delay medium for 1 day. After incubation, bombarded leaves are cut into approximately 0.5 cm$^2$ pieces and placed abaxial side up on TSO medium supplemented with a sublethal concentration of glyphosate (10 $\mu$M), the 3 essential aromatic amino acids at 100 nM each and 3 mg/L BAP. The leaf segments were on the 10 $\mu$M glyphosate medium for 3 weeks and were then transferred to medium containing a lethal concentration of glyphosate (100 $\mu$M). A total of seven transgenic shoots were obtained approximately 4 to 10 weeks after the leaves were transferred to 100 $\mu$M glyphosate.

DNA from the seven putative transgenic shoots was isolated and analyzed by Southern blot hybridization. Using a plastid DNA probe and diagnostic restriction enzyme digestions, the chimeric CP4 (and aadA) genes in pMON38789 were shown to be integrated into the tobacco plastid genome. All seven plantlets were transplastomic and heteroplasmic by this criteria. The plantlets were allowed to regenerate new shoots on regeneration medium containing 100 $\mu$M glyphosate. New shoots were tested for homoplasmy by Southern blot analysis as described above.

Figure 17:
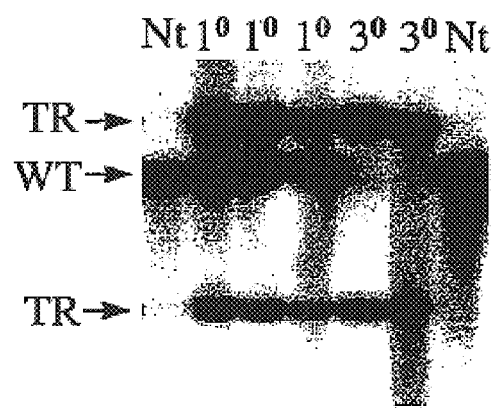
FIG. 17 provides the results of Southern blot hybridizations of plastid transformed tobacco lines directly selected on medium containing glyphosate. All seven lines tested contain the introduced plastid lethal construct.

Of the total of 7 glyphosate resistant lines that were obtained, all 7 have been confirmed to carry the CP4 gene by Southern blot analysis, as shown in FIG. 17. The primary transformed lines were all heteroplasmic with a mixture of wild-type genomes and CP4+ genomes. Upon two additional plant regenerations (tertiary clones), homoplasmy to CP4+ was obtained in all of the lines tested.

The above results indicate that the methods described herein are useful for obtaining plastid transformed plants through selection on medium having plastid lethal compounds. In addition, the methods are useful for the plastid transformation of plants to produce transplastomic lines that lack an antibiotic selectable marker. Furthermore, the methods are useful for the production of transplastomic plants that are capable of being selected by resistance to glyphosate or phosphinothricin. The methods of the present invention are applicable to a wide number of plant species.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for obtaining a transplastomic plant, wherein the method comprises the steps of:
    a) introducing into a plastid of a plant cell a recombinant nucleic acid construct comprising regions of plastid homology, a promoter functional in a plant cell plastid, a nucleic acid sequence encoding a glyphosate resistant EPSPS, and a transcriptional termination region functional in a plant cell plastid to produce a transformed plant cell,
    b) placing said transformed plant cell on a first culture medium comprising a sublethal amount of glyphosate for a period of time sufficient to permit said plant cell to replicate to produce replicated plant cells, and
    c) placing said replicated plant cells on a second culture medium comprising a lethal concentration of glyphosate for a period of time sufficient to select plant cells capable of growing in the presence of glyphosate; and
    d) regenerating a transplastomic plant from said plant cells that grow in said second culture medium.

2. The method according to claim 1, wherein said glyphosate resistant EPSPS is CP4.

3. The method according to claim 1, wherein said plant cell is selected on said first culture medium for less than about 12 weeks.

4. The method according to claim 1, wherein said plant cell is selected on said first culture medium for less than about 8 weeks.

5. The method according to claim 1, wherein said plant cell is selected on said first culture medium for less than about 4 weeks.

6. The method according to claim 1, wherein said plant cell is selected on said first culture medium for less than about 3 weeks.

* * * * *

SEQUENCE LISTING

<160> NUMBER OF SEQ ID NOS: 2

<210> SEQ ID NO 1
<211> LENGTH: 202
<212> TYPE: DNA

-continued

```
<213> ORGANISM: Artificial Sequence
<220> FEATURE:
<223> OTHER INFORMATION: synthetic construct

<400> SEQUENCE: 1
gaattcggta cccccgtcgt tcaatgagaa tggataagag gctcgtggga ttgacgtgag      60
ggggcaggga tggctatatt tctgggagcg aactccgggc gaatactgaa gcgcttggat     120
acaagttatc cttggaagga aagacaattc cggatcctct agaaataatt ttgtttaact     180
ttaagaagga gatataccca tg                                              202

<210> SEQ ID NO 2
<211> LENGTH: 244
<212> TYPE: DNA
<213> ORGANISM: Artificial Sequence
<220> FEATURE:
<223> OTHER INFORMATION: synthetic construct

<400> SEQUENCE: 2
gaattcggta cccccgtcgt tcaatgagaa tggataagag gctcgtggga ttgacgtgag      60
ggggcaggga tggctatatt tctgggagcg aactccgggc gaatactgaa gcgcttggat     120
acaagttatc cttggaagga aagacaattc cggatcctct agaaataatt ttgtttaact     180
ttaagaagga gatataccca tgggtaaagg agaagaactt ttcactggag ttgtcccaag     240
catg                                                                  244
```